United States Patent [19]
Chappell et al.

[11] Patent Number: 5,365,017
[45] Date of Patent: * Nov. 15, 1994

[54] METHOD AND COMPOSITION FOR INCREASING STEROL ACCUMULATION IN HIGHER PLANTS

[75] Inventors: Joseph Chappell, Lexington, Ky.; Court A. Saunders, Clarendon Hills; Fred R. Wolf, Naperville, both of Ill.; Richard E. Cuellar, Glen Ellyn, Ill.

[73] Assignee: Amoco Corporation, Naperville, Ill.

[*] Notice: The portion of the term of this patent subsequent to Apr. 26, 2011 has been disclaimed.

[21] Appl. No.: 119,263

[22] Filed: Sep. 9, 1993

Related U.S. Application Data

[62] Division of Ser. No. 596,467, Oct. 12, 1990, Pat. No. 5,306,862.

[51] Int. Cl.$^5$ .................... A01H 1/04; C12N 15/00; C12N 9/02; C07H 21/04
[52] U.S. Cl. .................... 800/205; 800/250; 800/255; 800/DIG. 15; 800/DIG. 26; 800/DIG. 27; 800/DIG. 40; 800/DIG. 43; 800/DIG. 44; 800/DIG. 47; 800/DIG. 55; 800/DIG. 56; 435/69.1; 435/70.1; 435/172.3; 435/156; 435/189; 536/23.2; 536/23.5; 536/24.1; 47/58
[58] Field of Search .................... 536/23.2, 23.5, 24.1; 800/205, 250, 255, DIG. 26, 27, 15, 40, 43, 44, 47, 55, 56; 435/69.1, 70.1, 172.3, 156, 189; 47/58

[56] References Cited
U.S. PATENT DOCUMENTS
5,306,862 4/1994 Chappell et al. .................... 800/205

OTHER PUBLICATIONS
Gil et al. 1985. Cell 41(1):249-258.
Chappell et al. 1989. Plant Cell Reports 8(1):48-52.
Vogeli et al. 1988. Plant Physiol. 88(4):1291-1296.
Downey et al. 1980. Biochem. Biophys. Res. Commun. 94(3):974-979.

*Primary Examiner*—David T. Fox
*Attorney, Agent, or Firm*—Norval B. Galloway

[57] ABSTRACT

A method of increasing sterol accumulation in a plant by increasing the copy number of a gene encoding a polypeptide having HMG-CoA reductase activity is disclosed. The copy number is preferably increased by transforming plants with a recombinant DNA molecule comprising a vector operatively linked to an exogenous DNA segment that encodes a polypeptide having HMG-CoA reductase activity, and a promoter suitable for driving the expression of said polypeptide. Also disclosed are a method of increasing cycloartenol accumulation in a plant, a method of increasing the resistance of plants to pests and the transformed plants themselves.

11 Claims, 23 Drawing Sheets

```
TGTATGTCTT GTCTTTCTCC TAAGGGGCGT AGGCTCATTG ATAACTCATG TCCTCACCTT         60

GCACTCCTTT TGGAATTATT TGGTTTGAGT GAAGAAGACC GGACCTTCGA GGTTCGCAAC        120

TTAAACAATA GACTTGTGAG GATCCAGGGA CCGAGTGGCT ACA ATG TTG TCA CGA         175
                                             Met Leu Ser Arg
                                              1

CTT TTC CGT ATG CAT GGC CTC TTT GTG GCC TCC CAT CCC TGG GAA GTT         223
Leu Phe Arg Met His Gly Leu Phe Val Ala Ser His Pro Trp Glu Val
 5                      10                      15                  20

ATT GTG GGG ACG GTG ACA CTT ACC ATC TGT ATG ATG TCC ATG AAC ATG         271
Ile Val Gly Thr Val Thr Leu Thr Ile Cys Met Met Ser Met Asn Met
            25                      30                      35

TTC ACT GGC AAC AAC AAG ATC TGT GGT GGG TGG AAT TAC GAG TGC CCA AAA     319
Phe Thr Gly Asn Asn Lys Ile Cys Gly Gly Trp Asn Tyr Glu Cys Pro Lys
        40                      45                      50

TTT GAG GAG GAT GTA TTG AGC AGT GAC ATC ATC ATC CTC ACC ATA ACA         367
Phe Glu Glu Asp Val Leu Ser Ser Asp Ile Ile Ile Leu Thr Ile Thr
55                      60                      65

CGG TGC ATC GCC ATC CTG TAC ATT TAC ATC CTG TAC TTC CAG AAC TTA CGT     415
Arg Cys Ile Ala Ile Leu Tyr Ile Tyr Ile Leu Tyr Phe Gln Asn Leu Arg
70                      75                      80
```

Figure 2-1

```
CAG CTT GGG TCG AAG TAT ATT TTA GGT ATT GCT GGC CTG TTC ACA ATT    463
Gln Leu Gly Ser Lys Tyr Ile Leu Gly Ile Ala Gly Leu Phe Thr Ile
 85                  90                  95                 100

TTC TCA AGT TTT GTC TTT AGT ACA GTC GTC ATT CAC TTC TTA GAC AAA    511
Phe Ser Ser Phe Val Phe Ser Thr Val Val Ile His Phe Leu Asp Lys
            105                 110                 115

GAA CTG ACG GGC TTA AAT GAA GCT TTG CCC TTT TTC CTG CTT TTG ATT    559
Glu Leu Thr Gly Leu Asn Glu Ala Leu Pro Phe Phe Leu Leu Leu Ile
        120                 125                 130

GAC CTT TCT AGA GCG AGT GCA CTA GCA AAG TTT GCC CTA AGT TCA AAC    607
Asp Leu Ser Arg Ala Ser Ala Leu Ala Lys Phe Ala Leu Ser Ser Asn
    135                 140                 145

TCT CAG GAT GAA GTA AGG GAA AAT ATA GCT CGC GGA ATG GCA ATT CTG    655
Ser Gln Asp Glu Val Arg Glu Asn Ile Ala Arg Gly Met Ala Ile Leu
150                 155                 160

GGC CCC ACA TTC ACC CTT GAT GCT CTT GTG GAA TGT CTT GTA ATT GGA    703
Gly Pro Thr Phe Thr Leu Asp Ala Leu Val Glu Cys Leu Val Ile Gly
165                 170                 175                 180

GTT GGC ACC ATG TCA GGG GTG CGT CAG CTT GAA ATC ATG TGC TTT        751
Val Gly Thr Met Ser Gly Val Arg Gln Leu Glu Ile Met Cys Phe
            185                 190                 195
```

Figure 2-2

```
GGC TGC ATG TCT GTG CTT GCC AAC TAC TTC GTG TTC ATG ACA TTT TTC    799
Gly Cys Met Ser Val Leu Ala Asn Tyr Phe Val Phe Met Thr Phe Phe
            200                 205                 210

CCA GCG TGT GTG TCC CTG GTC CTT GAG CTT TCT CGG GAA AGT CGA GAG    847
Pro Ala Cys Val Ser Leu Val Leu Glu Leu Ser Arg Glu Ser Arg Glu
            215                 220                 225

GGT CGT CCA ATT TGG CAG CTT AGC CAT TTT GCC CGA GTT TTG GAA GAA    895
Gly Arg Pro Ile Trp Gln Leu Ser His Phe Ala Arg Val Leu Glu Glu
        230                 235                 240

GAA GAG AAT AAA CCA AAC CCT GTA ACC CAA AGG GTC AAG ATG ATT ATG    943
Glu Glu Asn Lys Pro Asn Pro Val Thr Gln Arg Val Lys Met Ile Met
245                 250                 255                 260

TCT TTA GGT TTG GTT CTT GTT CAT GCT CAC AGT CGA TGG ATA GCT GAT    991
Ser Leu Gly Leu Val Leu Val His Ala His Ser Arg Trp Ile Ala Asp
            265                 270                 275

CCT TCC CCT CAG AAT AGC ACA GAA CAT TCT AAA GTC TCC TTG GGA       1039
Pro Ser Pro Gln Asn Ser Thr Glu His Ser Lys Val Ser Leu Gly
            280                 285                 290

CTG GAT GAA GAT GTG TCC AAG AGA ATT GAA CCA AGT GTT TCT CTC TGG   1087
Leu Asp Glu Asp Val Ser Lys Arg Ile Glu Pro Ser Val Ser Leu Trp
            295                 300                 305
```

Figure 2-3

```
CAG TTT TAT CTC TCC AAG ATG ATC AGC ATG GAC ATT GAA CAA GTG GTT      1135
Gln Phe Tyr Leu Ser Lys Met Ile Ser Met Asp Ile Glu Gln Val Val
310                     315                 320

ACC CTG AGC TTA GCT TTT CTG TTG GCT GTC AAG TAC ATT TTC TTT GAA      1183
Thr Leu Ser Leu Ala Phe Leu Leu Ala Val Lys Tyr Ile Phe Phe Glu
325                 330                 335                 340

CAA GCA GAG ACA GAG TCC ACA CTG TCT TTA AAA AAT CCT ATC ACG TCT      1231
Gln Ala Glu Thr Glu Ser Thr Leu Ser Leu Lys Asn Pro Ile Thr Ser
        345                 350                 355

CCT GTC ACC GTG CTT GTG AAA GCT CCA GAC AAC TGT TGT AGA CGG GAG      1279
Pro Val Thr Val Leu Val Lys Ala Pro Asp Asn Cys Cys Arg Arg Glu
        360                 365                 370

CCT CTG CTT GTG AGA AGG AGC GAG AAG CTT TCA TCG GTT GAG GAG GAG      1327
Pro Leu Leu Val Arg Arg Ser Glu Lys Leu Ser Ser Val Glu Glu Glu
        375                 380                 385

CCT GGG GTG AGC CAA GAT AGA AGG AAA GTT GAG ATA AAA CCA TTA GTG      1375
Pro Gly Val Ser Gln Asp Arg Arg Lys Val Glu Ile Lys Pro Leu Val
390                 395                 400

GTG GAA ACT GAG AGT GCA AGC AGA GCT ACA TTT GTG CTT GGC GCC TCT      1423
Val Glu Thr Glu Ser Ala Ser Arg Ala Thr Phe Val Leu Gly Ala Ser
405                 410                 415                 420
```

Figure 2-4

```
GGG ACC AGC CCT CCA GTG GCA GCG AGG ACA CAG GAG CTT GAA ATT GAA    1471
Gly Thr Ser Pro Pro Val Ala Ala Arg Thr Gln Glu Leu Glu Ile Glu
                425                 430                 435

CTC CCC AGT GAG CCT CGG CCT AAT GAA GAA CTT GCA GAG ATA CTG GAG    1519
Leu Pro Ser Glu Pro Arg Pro Asn Glu Glu Leu Ala Glu Ile Leu Glu
                440                 445                 450

AGT GCC GAG AAA GGT GCA AAG TTC CTT AGC GAT GCA GAG ATC ATC CAG    1567
Ser Ala Glu Lys Gly Ala Lys Phe Leu Ser Asp Ala Glu Ile Ile Gln
                455                 460                 465

TTG GTC AAT GCC AAG CAC ATC CCA GCC TAC AAA TTG GAA ACC TTA ATG    1615
Leu Val Asn Ala Lys His Ile Pro Ala Tyr Lys Leu Glu Thr Leu Met
                470                 475                 480

GAA ACT CAT GAA CGT GGT GTA TCT ATT CGC CGG CAG CTC CTC TCC ACA    1663
Glu Thr His Glu Arg Gly Val Ser Ile Arg Arg Gln Leu Leu Ser Thr
                485                 490                 495                 500

AAG CTT CCA GAG CCT TCT TCT CTG CAG TAC CTG CCT TAC AGA GAT TAT    1711
Lys Leu Pro Glu Pro Ser Ser Leu Gln Tyr Leu Pro Tyr Arg Asp Tyr
                505                 510                 515

AAT TAT TCC CTG GTG ATG GGA GCT TGC TGT GAG AAT GTG ATC GGA TAT    1759
Asn Tyr Ser Leu Val Met Gly Ala Cys Cys Glu Asn Val Ile Gly Tyr
                520                 525                 530
```

Figure 2-5

```
ATG CCC ATC CCT GTC GGA GTA GCA GGG CCT CTG TGC CTG GAT GGT AAA    1807
Met Pro Ile Pro Val Gly Val Ala Gly Pro Leu Cys Leu Asp Gly Lys
        535                 540                 545

GAG TAC CAG GTT CCA ATG GCA ACA ACG GAA GGC TGT CTG GTG GCC AGC    1855
Glu Tyr Gln Val Pro Met Ala Thr Thr Glu Gly Cys Leu Val Ala Ser
        550                 555                 560

ACC AAC AGA GGC TGC AGG GCA ATA GGT CTT GGT GGA GGT GCC AGC AGC    1903
Thr Asn Arg Gly Cys Arg Ala Ile Gly Leu Gly Gly Gly Ala Ser Ser
        565                 570                 575         580

CGG GTC CTT GCA GAT GGG ATG ACC CGG GGC CCA GTG CGT CTT CCT        1951
Arg Val Leu Ala Asp Gly Met Thr Arg Gly Pro Val Val Arg Leu Pro
        585                 590                 595

CGT GCT TGT GAT TCT GCA GAA GTG AAG GCC TGG CTT GAA ACA CCC GAA    1999
Arg Ala Cys Asp Ser Ala Glu Val Lys Ala Trp Leu Glu Thr Pro Glu
        600                 605                 610

GGG TTT GCG GTG ATA AAG GAC GCC TTC GAT AGC ACT AGC AGA TTT GCA    2047
Gly Phe Ala Val Ile Lys Asp Ala Phe Asp Ser Thr Ser Arg Phe Ala
        615                 620                 625

CGT CTA CAG AAG CTT CAT GTG ACC ATG GCA GGG CGC AAC CTG TAC ATC    2095
Arg Leu Gln Lys Leu His Val Thr Met Ala Gly Arg Asn Leu Tyr Ile
        630                 635                 640
```

Figure 2-6

```
CGT TTC CAG TCC AAG ACA GGG GAT GCC ATG GGG ATG AAC ATG ATT TCC    2143
Arg Phe Gln Ser Lys Thr Gly Asp Ala Met Gly Met Asn Met Ile Ser
645                 650                 655                 660

AAG GGC ACT GAG AAA GCA CTT CTG AAG CTT CAG GAG TTC CCT GAA        2191
Lys Gly Thr Glu Lys Ala Leu Leu Lys Leu Gln Glu Phe Pro Glu
            665                 670                 675

ATG CAG ATT CTG GCA GTT AGT GGT AAC TAC TGC ACT GAC AAG AAA CCT    2239
Met Gln Ile Leu Ala Val Ser Gly Asn Tyr Cys Thr Asp Lys Lys Pro
                680                 685                 690

GCC GCC ATA AAC TGG ATC GAG ATT GGA AGA GGA AAG ACA GTT GTG TGT GAA 2287
Ala Ala Ile Asn Trp Ile Glu Ile Glu Arg Gly Lys Thr Val Val Cys Glu
    695                 700                 705

GCT GTT ATT CCA GCC AAG GTG AGA GAA GTA TTA AAG ACA ACT ACG        2335
Ala Val Ile Pro Ala Lys Val Arg Glu Val Leu Lys Thr Thr Thr
710                 715                 720

GAA GCT ATG ATT GAC AAC AAG AAT ATT GTG CTT GGT TCT GCC            2383
Glu Ala Met Ile Asp Val Asn Lys Asn Ile Val Leu Gly Ser Ala
725                 730                 735                 740

ATG GCT GGG AGC ATA GGA GGC TAC AAT GCC CAT GCA GCA AAC ATC GTC    2431
Met Ala Gly Ser Ile Gly Gly Tyr Asn Ala His Ala Ala Asn Ile Val
            745                 750                 755
```

Figure 2-7

```
ACT GCT ATC TAC ATT GCA TGT GGC CAG GAT GCA GCA CAG AAT GTG GGG    2479
Thr Ala Ile Tyr Ile Ala Cys Gly Gln Asp Ala Ala Gln Asn Val Gly
         760                 765                 770

AGT TCA AAC TGT ATT ACT TTA ATG GAA GCA AGT GGT CCC ACG AAT GAA    2527
Ser Ser Asn Cys Ile Thr Leu Met Glu Ala Ser Gly Pro Thr Asn Glu
         775                 780                 785

GAC TTG TAT ATC AGC TGC ACC ATG CCA TCT ATA GAG ATA GGA ACT GTG    2575
Asp Leu Tyr Ile Ser Cys Thr Met Pro Ser Ile Glu Ile Gly Thr Val
         790                 795                 800

GGT GGG ACC AAC CTC CTA CCA CAG CAG GCC TGT CTG CAG ATG CTA        2623
Gly Gly Gly Thr Asn Leu Leu Pro Gln Gln Ala Cys Leu Gln Met Leu
805                 810                 815                 820

GGT GTT CAA GGA GCG TGC AAA GAC AAT CCT GGA GAA AAT GCA CGG CAA    2671
Gly Val Gln Gly Ala Cys Lys Asp Asn Pro Gly Glu Asn Ala Arg Gln
         825                 830                 835

CTT GCC CGA ATT GTG TGT GGT ACT GTA ATG GCT GGG GAG TTG TCC TTG    2719
Leu Ala Arg Ile Val Cys Gly Thr Val Met Ala Gly Glu Leu Ser Leu
         840                 845                 850

ATG GCA GCA TTG GCA GGA CAT CTT GTT AGA AGT CAC ATG GTT CAT        2767
Met Ala Ala Leu Ala Gly His Leu Val Arg Ser His Met Val His
         855                 860                 865
```

Figure 2-8

```
AAC AGA TCG AAG ATA AAT TTA CAA GAT CTG CAA GGA ACG TGC ACC AAG      2815
Asn Arg Ser Lys Ile Asn Leu Gln Asp Leu Gln Gly Thr Cys Thr Lys
        870                     875                     880

AAG TCA GCT TGAGCAGCCT GACAGTATTG AACTGAAACA CGGGCATTGG              2864
Lys Ser Ala
885

GTTCTCAAGG ACTAACATGA AATCTGTGAA TTAAAAATCT CAATGCAGTG TCTTGTGGAA    2924

GATGAATGAA CGTGATCAGT GAGACGCCTG CTTGGTTTCT GGCTCTTTCA GAGACGTCTG    2984

AGGTCCTTTG CTCGGAGACT CCTCAGATCT GGAAACAGTG TGGTCCTTCC CATGCTGTAT    3044

TCTGAAAAGA TCTCATATGG ATGTTGTGCT CTGAGCACCA CAGATGTGAT CTGCAGCTCG    3104

TTTCTGAAAT GATGGAGTTC ATGGTGATCA GTGTGAGACT GGCCTCTCCC AGCAGGTTAA    3164

AAATGGAGTT TTAAATTATA CTGTAGCTGA CAGTACTTCT GATTTTATAT TTATTTAGTC    3224

TGAGTTGTAG AACTTTGCAA TCTAAGTTTA TTTTTTGTAA CCTAATAATT CATTTGGTGC    3284

TGGTCTATTG ATTTTTGGGG GTAAACAATA TTATTCTTCA GAAGGGACC TACTTCTTCA    3344

TGGGAAGAAT TACTTTTATT CTCAAACTAC AGAACAATGT GCTAAGCAGT GCTAAATTGT    3404

TCTCATGAAG AAAACAGTCA CTGCATTTAT CTCCGTAGGC CTTTTTTCAG AGAGGCCTTG    3464
```

Figure 2-9

| | | | | |
|---|---|---|---|---|
| TCTAGATTTT | TGCCAGCTAG | GCTACTGCAT | GTCTTAGTGT | CAGGCCTTAG | GAAAGTGCCA | 3524 |
| CGCTCTGCAC | TAAAGATATC | AGAGCTCTTG | GTGTTACTTA | GACAAGAGTA | TGAGCAAGTC | 3584 |
| GGACCTCTCA | GAGTGTGGGA | ACACAGTTTT | GAAAGAAAAA | CCATTTCTCT | AAGCCAATTT | 3644 |
| TCTTAAAGA | CATTTTAACT | TATTTAGCTG | AGTTCTAGAT | TTTTCGGGTA | AACTATCAAA | 3704 |
| TCTGTATATG | TTGTAATAAA | GTGTCTTATG | CTAGGAGTTT | ATTCAAAGTG | TTTAAGTAAT | 3764 |
| AAAGGACTC | AAATTTACAC | TGATAAAATA | CTCTAGCTTG | GGCCAGAGAA | GACAGTGCTC | 3824 |
| ATTAGCGTTG | TCCAGGAAAC | CCTGCTTGCT | TGCCAAGCCT | AATGAAGGGA | AAGTCAGCTT | 3884 |
| TCAGAGCCAA | TGATGGAGGC | CACATGAATG | GCCCTGGAGC | TGTGTGCCTT | GTTCTGTGGC | 3944 |
| CAGGAGCTTG | GTGACTGAAT | CATTTACGGG | CTCCTTTGAT | GGACCCATAA | AAGCTCTTAG | 4004 |
| CTTCCTCAGG | GGGTCAGCAG | AGTTGTTGAA | TCTTAATTTT | TTTTTAATG | TACCAGTTTT | 4064 |
| GTATAAATAA | TAATAAAGAG | CTCCTTATTT | TGTATTCTAT | CTAATGCTTC | GAGTTCAGTC | 4124 |
| TTGGGAAGCT | GACATCTCAT | GTAGAAGATG | GACTCTGAAA | GACATTCCAA | GAGTGCAGCG | 4184 |
| GCATCATGGG | AGCCTCTTAG | TGATTGTGTG | TCAGTATTAT | TGTGGAAGAT | TGACTTTGCT | 4244 |
| TTTGTATGTG | AAGTTTCAGA | TTGCTCCCTCT | TGTGACTTTT | TAGCCAGTAA | CATTTTATTT | 4304 |

Figure 2-10

```
ACCTGAGCTT GTCATGGAAG TGGCAGTGAA AAGTATTGAG TATTCATGCT GGTGACTGTA    4364

ACCAATGTCA TCTTGCTAAA AACTCATGTT TTGTACAATT ACTAAATTGT ATACATTTTG    4424

TTATAGAATA CTTTTTCCAG TTGAGTAAAT TATGAAAGGA AGTTAACATT AACAGGTGTA    4484

AGCGGTGGCT TTTTAAAAT GAAGGATTAA CCCTAAGCCC GAGACCCAGA AGCTAGCAAA     4544

GTCTGGCAGA GTGGTAAACT GTCCTGCTGG GGCCATCCAA TCATCTCTCT CCATTACACT    4604

TTCTAACTTT GCAGCATTGG TGCTGGCCAG TGTATTGTTT CATTGATCTT CCTTACGCTT    4664

AGAGGGTTTG ATTGGTTCAG ATCTATAATC TCAGCCACAT TGTCTTGGTA TCAGCTGGAG    4724

AGAGTTAAGA GGAAGGGAAA ATAAAGTTCA GATAGCCAAA ACAC                     4768
```

Figure 2-11

```
TTTATTAACT TATTTTTTC TTCTTTCTAC CCAATTCTAG TCAGGAAAAG ACTAAGGGCT         60

GGAACATAGT GTATCATTGT CTAATTGTTG ATACAAGTA GATAAATACA TAAAACAAGC        120

ATG CCG CCG CTA TTC AAG GGA CTG AAA CAG ATG GCA AAG CCA ATT GCC        168
Met Pro Pro Leu Phe Lys Gly Leu Lys Gln Met Ala Lys Pro Ile Ala
 1                   5                  10                  15

TAT GTT TCA AGA TTT TCG GCG AAA CGA CCA ATT CAT ATA ATA CTT TTT        216
Tyr Val Ser Arg Phe Ser Ala Lys Arg Pro Ile His Ile Ile Leu Phe
                20                  25                  30

TCT CTA ATC ATA TCC GCA TTC GCT TAT CTA TCC GTC ATT CAG TAT TAC        264
Ser Leu Ile Ile Ser Ala Phe Ala Tyr Leu Ser Val Ile Gln Tyr Tyr
        35                  40                  45

TTC AAT GGT TGG CAA CTA GAT TCA AAT AGT GTT TTT GAA ACT GCT CCA        312
Phe Asn Gly Trp Gln Leu Asp Ser Asn Ser Val Phe Glu Thr Ala Pro
    50                  55                  60

AAT AAA GAC TCC AAC ACT CTA TTT CAA GAA TGT TCC CAT TAC TAC AGA        360
Asn Lys Asp Ser Asn Thr Leu Phe Gln Glu Cys Ser His Tyr Tyr Arg
65                  70                  75                  80

GAT TCC TCT CTA GAT GGT TGG GTA TCA ATC ACC GCG CAT GAA GCT AGT        408
Asp Ser Ser Leu Asp Gly Trp Val Ser Ile Thr Ala His Glu Ala Ser
                85                  90                  95
```

Figure 3-1

```
GAG TTA CCA GCC CCA CAC CAT TAC TAT CTA TTA AAC CTG AAC TTC AAT      456
Glu Leu Pro Ala Pro His His Tyr Tyr Leu Leu Asn Leu Asn Phe Asn
            100                 105                 110

AGT CCT AAT GAA ACT GAC TCC ATT CCA GAA CTA GCT AAC ACG GTT TTT      504
Ser Pro Asn Glu Thr Asp Ser Ile Pro Glu Leu Ala Asn Thr Val Phe
        115                 120                 125

GAG AAA GAT AAT ACA AAA TAT ATT CTG CAA GAA GAT CTC AGT GTT TCC      552
Glu Lys Asp Asn Thr Lys Tyr Ile Leu Gln Glu Asp Leu Ser Val Ser
    130                 135                 140

AAA GAA ATT TCT ACT GAT GGA ACG AAA TGG AGG TTA AGA AGT GAC          600
Lys Glu Ile Ser Thr Asp Gly Thr Lys Trp Arg Leu Arg Ser Asp
145                 150                 155                 160

AGA AAA CTT TTC GAC GTA AAG ACG TTA GCA TAT TCT CTC TAC GAT          648
Arg Lys Leu Phe Asp Val Lys Thr Leu Ala Tyr Ser Leu Tyr Asp
            165                 170                 175

GTA TTT TCA GAA AAT GTA ACC CAA GAC GCA GAC CCG TTT GAC GTC CTT ATT  696
Val Phe Ser Glu Asn Val Thr Gln Ala Asp Pro Phe Asp Val Leu Ile
        180                 185                 190

ATG GTT ACT GCC TAC CTA ATG ATG TTC TAC ACC ATA TTC GGC CTC TTC      744
Met Val Thr Ala Tyr Leu Met Met Phe Tyr Thr Ile Phe Gly Leu Phe
    195                 200                 205
```

Figure 3-2

| | | | | | | | | | | | | | | | | |
|---|---|---|---|---|---|---|---|---|---|---|---|---|---|---|---|---|
| AAT | GAC | ATG | AGG | AAG | ACC | GGG | TCA | AAT | TTT | TGG | TTG | AGC | GCC | TCT | ACA | 792 |
| Asn | Asp | Met | Arg | Lys | Thr | Gly | Ser | Asn | Phe | Trp | Leu | Ser | Ala | Ser | Thr | |
| 210 | | | | | | 215 | | | | | 220 | | | | | |
| GTG | GTC | AAT | TCT | GCA | TCA | CTT | TTC | TTA | GCA | TTG | TAT | GTC | ACC | CAA | | 840 |
| Val | Val | Asn | Ser | Ala | Ser | Leu | Phe | Leu | Ala | Leu | Tyr | Val | Thr | Gln | | |
| 225 | | | | 230 | | | | | 235 | | | | | 240 | | |
| TGT | ATT | CTA | GGC | AAA | GAA | GTT | TCC | GCA | TTA | ACT | CTT | TTT | GAA | GGT | TTG | 888 |
| Cys | Ile | Leu | Gly | Lys | Glu | Val | Ser | Ala | Leu | Thr | Leu | Phe | Glu | Gly | Leu | |
| | | | | 245 | | | | | 250 | | | | | | 255 | |
| CCT | TTC | ATT | GTA | GTT | GTT | GGT | TTC | AAG | CAC | AAA | ATC | AAG | ATT | GCC | | 936 |
| Pro | Phe | Ile | Val | Val | Val | Gly | Phe | Lys | His | Lys | Ile | Lys | Ile | Ala | | |
| | | 260 | | | | | 265 | | | | 270 | | | | | |
| CAG | TAT | GCC | CTG | GAG | AAA | TTT | GAA | AGA | GTC | GGT | TTA | TCT | AAA | AGG | ATT | 984 |
| Gln | Tyr | Ala | Leu | Glu | Lys | Phe | Glu | Arg | Val | Gly | Leu | Ser | Lys | Arg | Ile | |
| | 275 | | | | | 280 | | | | | 285 | | | | | |
| ACT | ACC | GAT | GAA | ATC | GTT | TTT | GAA | TCC | GTG | AGC | GAA | GAG | GGT | GGT | CGT | 1032 |
| Thr | Thr | Asp | Glu | Ile | Val | Phe | Glu | Ser | Val | Ser | Glu | Glu | Gly | Gly | Arg | |
| | 290 | | | | | 295 | | | | 300 | | | | | | |
| TTG | ATT | CAA | GAC | CAT | TTG | CTT | TGT | ATT | TTT | GCC | TTT | ATC | GGA | TGC | TCT | 1080 |
| Leu | Ile | Gln | Asp | His | Leu | Leu | Cys | Ile | Phe | Ala | Phe | Ile | Gly | Cys | Ser | |
| 305 | | | | 310 | | | | | 315 | | | | | 320 | | |

Figure 3-3

```
ATG TAT GCT CAC CAA TTG AAG ACT TTG ACA AAC TTC TGC ATA TTA TCA   1128
Met Tyr Ala His Gln Leu Lys Thr Leu Thr Asn Phe Cys Ile Leu Ser
            325                 330                 335

GCA TTT ATC CTA ATT TTT GAA TTG ATT TTA ACT CCT ACA TTT TAT TCT   1176
Ala Phe Ile Leu Ile Phe Glu Leu Ile Leu Thr Pro Thr Phe Tyr Ser
            340                 345                 350

GCT ATC TTA GCG CTT AGA CTG GAA ATG AAT GTT ATC CAC AGA TCT ACT   1224
Ala Ile Leu Ala Leu Arg Leu Glu Met Asn Val Ile His Arg Ser Thr
            355                 360                 365

ATT ATC AAG CAA ACA TTA GAA GAA GAC GGT GTT CCA GTT GTT ACA GCA   1272
Ile Ile Lys Gln Thr Leu Glu Glu Asp Gly Val Pro Val Val Thr Ala
            370                 375                 380

AGA ATC ATT TCT AAA GCA GAA GAA AAG AAA TCC GTA TCT TCT TTA AAT   1320
Arg Ile Ile Ser Lys Ala Glu Glu Lys Lys Ser Val Ser Phe Leu Asn
 385                390                 395                 400

CTC AGT GTG GTT GTC ATT ATG AAA CTC TCT GTC ATA CTG TTG TTT       1368
Leu Ser Val Val Val Ile Met Ile Lys Leu Leu Ser Val Ile Leu Phe
            405                 410                 415

GTT TTC ATC AAC TTT TAT AAC TTT GGT GCA AAT TGG GTC AAT GAT GCC   1416
Val Phe Ile Asn Phe Tyr Asn Phe Gly Ala Asn Trp Val Asn Asp Ala
            420                 425                 430
```

Figure 3-4

| | | | | | | | | | | | | | | | |
|---|---|---|---|---|---|---|---|---|---|---|---|---|---|---|---|
| TTC | AAT | TCA | TTG | TAC | TTC | GAT | AAG | GAA | CGT | GTT | TCT | CTA | CCA | GAT | TTT | 1464
| Phe | Asn | Ser | Leu | Tyr | Phe | Asp | Lys | Glu | Arg | Val | Ser | Leu | Pro | Asp | Phe |
| | | 435 | | | | | 440 | | | | | 445 | | | |

ATT ACC TCG AAT GCC TCT GAA AAC TTT AAA GAG CAA GCT ATT GTT AGT 1512
Ile Thr Ser Asn Ala Ser Glu Asn Phe Lys Glu Gln Ala Ile Val Ser
    450                 455                 460

GTC ACC CCA TTA TAT TAC AAA CCC ATT AAG TCC TAC CAA CGC ATT 1560
Val Thr Pro Leu Tyr Tyr Lys Pro Ile Lys Ser Tyr Gln Arg Ile
465             470             475             480

GAG GAT ATG GTT CTT CGT AAT GTC AGT GTT GCC ATT CGT 1608
Glu Asp Met Val Leu Arg Asn Val Ser Val Ala Ile Arg
        485                 490                 495

GAT AGG TTC GTC AGT AAA TTA GTT CTT TCC GCC TTA GTA TGC AGT GCT 1656
Asp Arg Phe Val Ser Lys Leu Val Leu Ser Ala Leu Val Cys Ser Ala
        500                 505                 510

GTC ATC AAT GTG TAT TTA TTG AAT GCT GCT AGA ATT CAT ACC AGT TAT 1704
Val Ile Asn Val Tyr Leu Leu Asn Ala Ala Arg Ile His Thr Ser Tyr
    515                 520                 525

ACT GCA GAC CAA TTG GTG AAA ACT GAA GTC ACC AAG AAG TCT TTT ACT 1752
Thr Ala Asp Gln Leu Val Lys Thr Glu Val Thr Lys Lys Ser Phe Thr
530                 535                 540

Figure 3-5

```
GCT CCT GTA CAA AAG GCT TCT ACA CCA GTT TTA ACC AAT AAA ACA GTC    1800
Ala Pro Val Gln Lys Ala Ser Thr Pro Val Leu Thr Asn Lys Thr Val
545                 550                 555                 560

ATT TCT GGA TCG AAA GTC AAA AGT TTA TCA TCT GCG CAA TCG AGC TCA    1848
Ile Ser Gly Ser Lys Val Lys Ser Leu Ser Ser Ala Gln Ser Ser Ser
            565                 570                 575

TCA GGA CCT TCA TCT AGT GAG GAA GAT GAT TCC CGC GAT ATT GAA        1896
Ser Gly Pro Ser Ser Ser Glu Glu Asp Asp Ser Arg Asp Ile Glu
        580                 585                 590

AGC TTG GAT AAG AAA ATA CGT CCT TTA GAA GAA TTA GCA TTA TTA        1944
Ser Leu Asp Lys Lys Ile Arg Pro Leu Glu Glu Leu Ala Leu Leu
    595                 600                 605

AGT AGT GGA AAT ACA AAA CAA TTG AAG AAC AAA GAG GTC GCT GCC TTG    1992
Ser Ser Gly Asn Thr Lys Gln Leu Lys Asn Lys Glu Val Ala Ala Leu
610                 615                 620

GTT ATT CAC GGT AAG TTA CCT TTG TAC GCT TTG GAG AAA TTA GGT        2040
Val Ile His Gly Lys Leu Pro Leu Tyr Ala Leu Glu Lys Leu Gly
625                 630                 635                 640

GAT ACT ACG AGA GCG GTT GCG GTA CGT AGG AAG GCT CTT TCA ATT TTG    2088
Asp Thr Thr Arg Ala Val Ala Val Arg Arg Lys Ala Leu Ser Ile Leu
                645                 650                 655
```

Figure 3-6

| | | | | | | | | | | | | | | | | |
|---|---|---|---|---|---|---|---|---|---|---|---|---|---|---|---|---|
| GCA | GAA | GCT | CCT | GTA | TTA | GCA | TCT | GAT | CGT | TTA | CCA | TAT | AAA | AAT | TAT | 2136 |
| Ala | Glu | Ala | Pro | Val | Leu | Ala | Ser | Asp | Arg | Leu | Pro | Tyr | Lys | Asn | Tyr | |
| | | | 660 | | | | | 665 | | | | | 670 | | | |
| GAC | TAC | GAC | CGC | GTA | TTT | GGC | GCT | TGT | TGT | GAA | AAT | GTT | ATA | GGT | TAC | 2184 |
| Asp | Tyr | Asp | Arg | Val | Phe | Gly | Ala | Cys | Cys | Glu | Asn | Val | Ile | Gly | Tyr | |
| | | | 675 | | | | | 680 | | | | | 685 | | | |
| ATG | CCT | TTG | CCC | GTT | GGT | GTT | ATA | GGC | CCC | TTG | GTT | ATC | GAT | GGT | ACA | 2232 |
| Met | Pro | Leu | Pro | Val | Gly | Val | Ile | Gly | Pro | Leu | Val | Ile | Asp | Gly | Thr | |
| | | | 690 | | | | | 695 | | | | | 700 | | | |
| TCT | TAT | CAT | ATA | CCA | ATG | GCA | ACT | ACA | GAG | GGT | TGT | TTG | GTA | GCT | TCT | 2280 |
| Ser | Tyr | His | Ile | Pro | Met | Ala | Thr | Thr | Glu | Gly | Cys | Leu | Val | Ala | Ser | |
| | | | 705 | | | | | 710 | | | | | 715 | | | 720 |
| GCC | ATG | CGT | GGC | TGT | AAG | GCA | ATC | AAT | GCT | GGC | GGT | GCA | ACA | ACT | ACT | 2328 |
| Ala | Met | Arg | Gly | Cys | Lys | Ala | Ile | Asn | Ala | Gly | Gly | Ala | Thr | Thr | Thr | |
| | | | | 725 | | | | | 730 | | | | | 735 | | |
| GTT | TTA | ACT | AAG | GAT | GGT | ATG | ACA | AGA | GGC | CCA | GTC | CGT | TTC | CCA | | 2376 |
| Val | Leu | Thr | Lys | Asp | Gly | Met | Thr | Arg | Gly | Pro | Val | Arg | Phe | Pro | | |
| | | | 740 | | | | | 745 | | | | | 750 | | | |
| ACT | TTG | AAA | AGA | TCT | GGT | GCC | TGT | AAG | ATA | TGG | TTA | GAC | TCA | GAA | GAG | 2424 |
| Thr | Leu | Lys | Arg | Ser | Gly | Ala | Cys | Lys | Ile | Trp | Leu | Asp | Ser | Glu | Glu | |
| | | | 755 | | | | | 760 | | | | | 765 | | | |

Figure 3-7

```
GGA CAA AAC GCA ATT AAA GCT TTT AAC TCT ACA TCA AGA TTT GCA     2472
Gly Gln Asn Ala Ile Lys Ala Phe Asn Ser Thr Ser Arg Phe Ala
        770             775             780

CGT CTG CAA CAT ATT CAA ACT TGT CTA GCA GGA GAT TTA CTC TTC ATG 2520
Arg Leu Gln His Ile Gln Thr Cys Leu Ala Gly Asp Leu Leu Phe Met
785             790             795             800

AGA TTT AGA ACA ACT GGT GAC GCA ATG GGT ATG AAT ATG ATT TCT     2568
Arg Phe Arg Thr Thr Gly Asp Ala Met Gly Met Asn Met Ile Ser
        805             810             815

AAA GGT GTC GAA TAC TCA TTA AAG CAA ATG GTA GAA GAG TAT GGC TGG 2616
Lys Gly Val Glu Tyr Ser Leu Lys Gln Met Val Glu Glu Tyr Gly Trp
820             825             830

GAA GAT ATG GAG GTT TCT GGT AAC TAC TGT ACC GAC AAA           2664
Glu Asp Met Glu Val Ser Gly Asn Tyr Cys Thr Asp Lys
    835             840             845

AAA CCA GCT GCC ATC AAC TGG ATC GAA GGT CGT GGT AAG AGT GTC GTC 2712
Lys Pro Ala Ala Ile Asn Trp Ile Glu Gly Arg Gly Lys Ser Val Val
850             855             860

GCA GAA GCT ACT ATT CCT GGT GAT GTT GTC AGA AAA GTG TTA AAA AGT 2760
Ala Glu Ala Thr Ile Pro Gly Asp Val Val Arg Lys Val Leu Lys Ser
865             870             875             880
```

Figure 3-8

```
GAT GTT TCC GCA TTG GTT GAG TTG AAC ATT GCT AAG AAT TTG GTT GGA         2808
Asp Val Ser Ala Leu Val Glu Leu Asn Ile Ala Lys Asn Leu Val Gly
            885                     890                     895

TCT GCA ATG GCT GTT GGG TCT GTT GGA GGA CAT GCA CAT GCA GCT AAT         2856
Ser Ala Met Ala Val Gly Ser Val Gly Gly Phe Asn Ala His Ala Asn
        900                     905                     910

TTA GTG ACA GCT GTT TTC TTG GCA TTA GGA CAA GAT CCT GCA CAA AAT         2904
Leu Val Thr Ala Val Phe Leu Ala Leu Gly Gln Asp Pro Ala Gln Asn
        915                     920                     925

GTT GAA AGT TCC AAC TGT ATA ACA TTG ATG AAA GAA GTG GAC GGT GAT         2952
Val Glu Ser Ser Asn Cys Ile Thr Leu Met Lys Glu Val Asp Gly Asp
        930                     935                     940

TTG AGA ATT TCC GTA TCC ATG CCA TCC ATC GAA GTA GGT ACC ATC GGT         3000
Leu Arg Ile Ser Val Ser Met Pro Ser Ile Glu Val Gly Thr Ile Gly
    945                     950                     955         960

GGT ACT GTT CTA GAA CCA CAA GGT GCC ATG TTG GAC TTA TTA GGT             3048
Gly Thr Val Leu Glu Pro Gln Gly Ala Met Leu Asp Leu Leu Gly
        965                     970                     975

GTA AGA GGC CCG CAT GCT ACC GCT CCT GGT ACC AAC GCA CGT CAA TTA         3096
Val Arg Gly Pro His Ala Thr Ala Pro Gly Thr Asn Ala Arg Gln Leu
        980                     985                     990
```

Figure 3-9

```
GCA AGA ATA GTT GCC TGT GCC GTC TTG GCA GGT GAA TTA TCC TTA TGT      3144
Ala Arg Ile Val Ala Cys Ala Val Leu Ala Gly Glu Leu Ser Leu Cys
         995                    1000                    1005

GCT GCC CTA GCA GCC GGC CAT TTG GTT CAA AGT CAT ATG ACC CAC AAC      3192
Ala Ala Leu Ala Ala Gly His Leu Val Gln Ser His Met Thr His Asn
         1010                   1015                   1020

AGG AAA CCT GCT GAA CCA ACA AAA CCT AAC AAT TTG GAC GCC ACT GAT      3240
Arg Lys Pro Ala Glu Pro Thr Lys Pro Asn Asn Leu Asp Ala Thr Asp
         1025                   1030                   1035   1040

ATA AAT CGT TTG AAA GAT GGG TCC GTC ACC TGC ATT AAA TCC              3282
Ile Asn Arg Leu Lys Asp Gly Ser Val Thr Cys Ile Lys Ser
         1045                   1050

TAAACTTAGT CATACGTCAT TGGTATTCTC TTGAAAAAGA AGCACAACAG CACCATGTGT    3342

TACGTAAAAT ATTTACTT                                                  3360
```

Figure 3-10

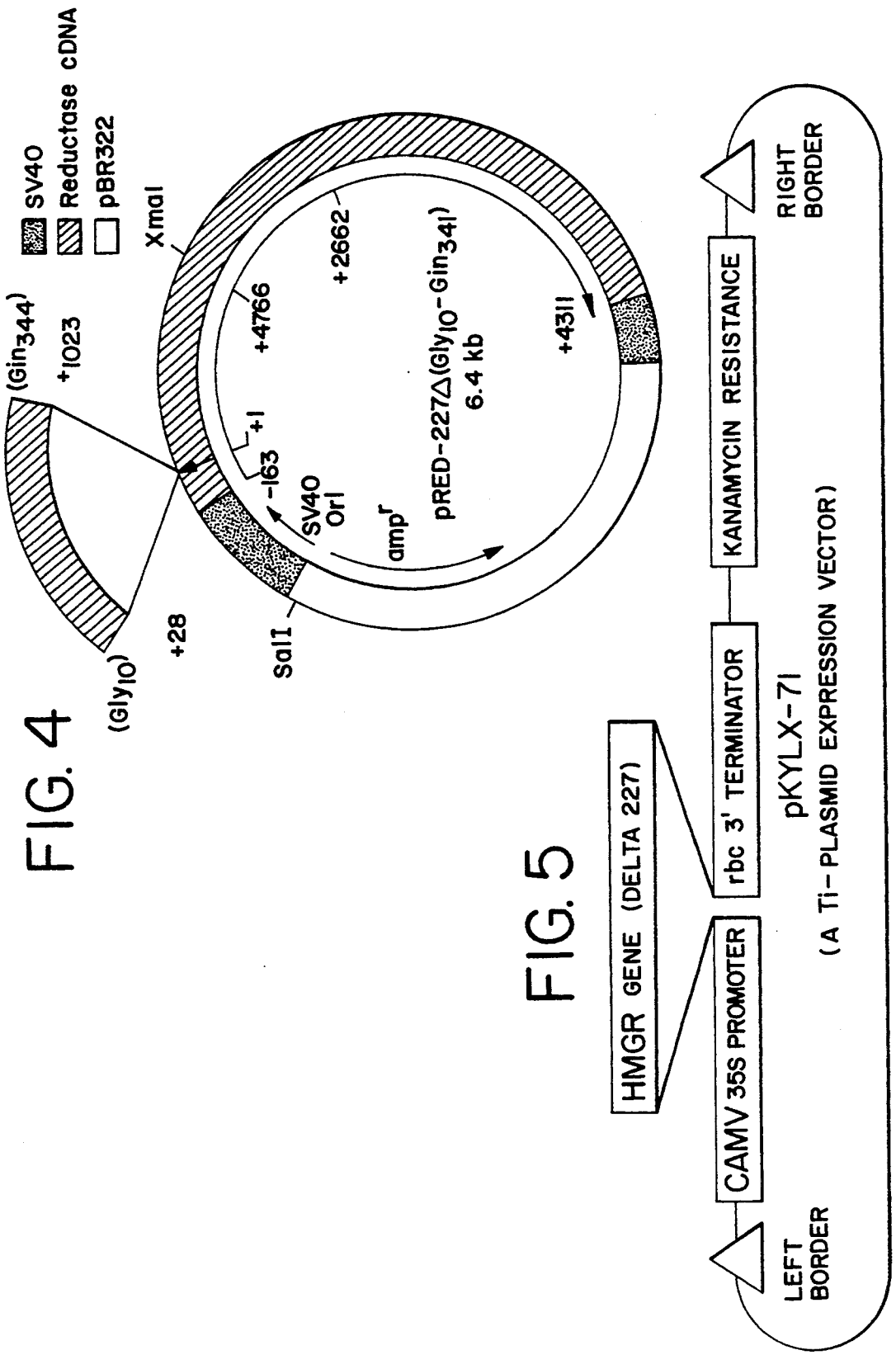

METHOD AND COMPOSITION FOR INCREASING STEROL ACCUMULATION IN HIGHER PLANTS

This is a divisional application of U.S. application Ser. No. 07/596,467, filed Oct. 12, 1990, now U.S. Pat. No. 5,306,862.

DESCRIPTION

1. Technical Field

The present invention relates to methods and compositions for increasing the accumulation of sterols in higher plants, and more particularly to increasing sterol accumulation by increasing the number of copies of a gene encoding a polypeptide having HMG-CoA reductase activity.

2. Background of the Invention

Mevalonate ($C_6H_{11}O_4$) is the metabolic precursor of a vast array of compounds vital for cell and organism viability. In plants, the major endproducts derived from mevalonate are the sterols and other isoprenoids. (see FIG. 1).

Exemplary plant isoprenoids include the terpenes (volatile $C_{10}$ and $C_{15}$ compounds giving rise to fragrances of many plants) the carotenoids ($C_{40}$ compounds giving rise to the color of many plants) and polymers such as natural rubber.

Free sterols are constituents of virtually all eukaryotic membranes. The most abundant sterols of vascular plants are campesterol, 24-methylcholesterol, sitosterol and stigmasterol.

Mevalonate is formed from the reduction of 3-hydroxy-3-methylglutaryl coenzyme A (HMG-CoA). The reduction of HMG-CoA to mevalonate is catalyzed by the enzyme HMG-CoA reductase.

The HMG-CoA reductase enzymes of animals and yeasts are integral membrane glycoproteins of the endoplasmic reticulum. The intact enzyme comprises three regions: a catalytic region, containing the active site of the enzyme, a membrane binding region, anchoring the enzyme to the endoplasmic reticulum and a linker region, joining the catalytic and membrane binding regions of the enzymes. The membrane binding region occupies the $NH_2$-terminal portion of the intact protein, whereas the catalytic region occupies the COOH-terminal portion of the protein, with the linker region constituting the remaining portion. Basson, M. E. et al., *Mol. Cell Biol.*, 8(9):3797–3808 (1988). At present, the subcellular localization of HMG-CoA reductase in plants is not known. Russell, D. W. et al., *Current Topics in Plant Biochemistry*, Vol. 4, ed. by D. D. Randall et al., Univ. of Missouri (1985).

The activity of HMG-CoA reductase in animals and yeasts is known to be subject to feedback inhibition by sterols. Such feedback inhibition requires the presence of the membrane binding region of the enzyme. See, e.g., Gil, G. et al., *Cell*, 41: 249–258(1985); Bard, M. and Downing, J. F. *Journal of General Microbiology*, 125:415–420(1981).

Given that mevalonate is the precursor for sterols and other isoprenoids, it might be expected that increases in the amount or activity of HMG-CoA reductase would lead to increases in the accumulation of both sterols and other isoprenoids. In yeasts and non-photosynthetic microorganisms, increases in HMG-CoA reductase activity are not associated with predictable increases in the production of sterols or other isoprenoids.

In mutant strains of the yeast *Saccharomyces cerevisiae* (*S. cerevisiae*) having abnormally high levels of HMG-CoA reductase activity, the production of two sterols, 4,14-dimethylzymosterol and 14-methylfecosterol, is markedly increased above normal. Downing, J. F. et al., *Biochemical and Biophysical Research Communications*, 94(3): 974–979(1980).

When HMG-CoA reductase activity was increased by illumination in non-photosynthetic microorganisms, isoprenoid (carotenoid), but not sterol (ergosterol), synthesis was enhanced. Tada, M. and Shiroishi, M. *Plant and Cell Physiology*, 23(4): 615–621(1982). There are no studies reporting the effects of such increases in HMG-CoA reductase activity in plants.

SUMMARY OF THE INVENTION

The present invention provides a method of increasing sterol accumulation in a plant that comprises increasing the copy number of a structural gene that encodes a polypeptide having HMG-CoA reductase activity, thereby increasing the activity of that enzyme relative to the activity in the native plant. A polypeptide having HMG-CoA reductase activity includes an intact HMG-CoA reductase enzyme as well as an active, truncated HMG-CoA reductase enzyme. In a preferred embodiment, an active, truncated HMG-CoA reductase enzyme comprises the catalytic and linker regions, but not the membrane binding region, of hamster HMG-CoA reductase.

The copy number of a gene encoding a polypeptide having HMG-CoA reductase activity is increased by transforming a plant with a recombinant DNA molecule comprising a vector operatively linked to an exogenous DNA segment that encodes a polypeptide having HMG-CoA reductase activity, and a promoter suitable for driving the expression of said polypeptide in the plant. A preferred recombinant DNA molecule is plasmid HMGRΔ227-pKYLX71.

The promoter is preferably a promoter whose regulatory function is substantially unaffected by the level of sterol in the transformed plant. A preferred promoter is the CaMV 35S promoter. In particularly preferred practice, the level of an accumulated sterol, cycloartenol, is particularly enhanced.

The present invention still further provides a method of increasing pest resistance in plants. In this method, the copy number of a structural gene that encodes a polypeptide having HMG-CoA reductase activity is increased over that of the native plant, as discussed before.

A transformed plant having an increased copy number of a structural gene that encodes a polypeptide having HMG-CoA reductase activity is also contemplated. Such a plant exhibits a higher total sterol, particularly cycloartenol, content than does a native, untransformed plant. Such a transformed plant also exhibits resistance to pests such as hornworm, relative to an untransformed plant, native plant.

The present invention further provides a plant seed capable of germinating into a plant that over accumulates sterol relative to a native, untransformed plant of the same strain and mutants, recombinants, genetically engineered derivatives thereof and hybrids derived therefrom.

BRIEF DESCRIPTION OF THE DRAWINGS

In the drawings forming a portion of this disclosure:

FIGS. 2-1 to 2-11 shown as eleven panels designated FIGS. 2-1 to 2-11, are a composite nucleotide sequence of the cDNA corresponding to the mRNA for hamster HMG-CoA reductase, and the predicted amino acid sequence of the protein as published by Chin, D. J. et al., *Nature*, 308:613–617 (1984). Nucleotides are numbered (left-hand side) in the 5' to 3' direction. Position 1 corresponds to the first nucleotide of the ATG triplet coding for the initiator methionine. The predicted amino acid sequence is shown below the nucleotide sequence. The amino acid residues are numbered (right-hand side) beginning with the initiator methionine.

FIGS. 3-1 to 3-10, shown as ten panels designated FIGS. 3-1 to 3-10, are the nucleotide base sequence and derived amino acid residue sequence for *S. cerevisiae* HMG-CoA reductase 1 published by Basson, M. E. et al., *Mol. Cell Biol.*, 8(9):3797–3808 (1988). Nucleotides are shown and numbered as discussed for FIG. 2 as are the derived amino acid residues.

FIG. 4 is a schematic drawing showing the structure of a plasmid (pRed-227Δ) used to insert a truncated hamster gene encoding for hamster HMG-CoA reductase into cells lacking such hamster enzyme. Base pairs of the reductase coding sequence (nucleotides 28 to 1023) that encode amino acids 10 to 341 have been deleted and are shown externally of the plasmid. The hatched area denotes the reductase cDNA sequence portion of the plasmid. The reductase cDNA initiator methionine codon (nucleotide 1) and terminator codon (nucleotide 2662) are indicated, as are other features of the plasmid.

FIG. 5 is a schematic restriction map of plasmid HMGRΔ227-pKYLX71 used to transform the plants of the present invention.

DETAILED DESCRIPTION OF THE INVENTION

I. Definitions

Figure 1:
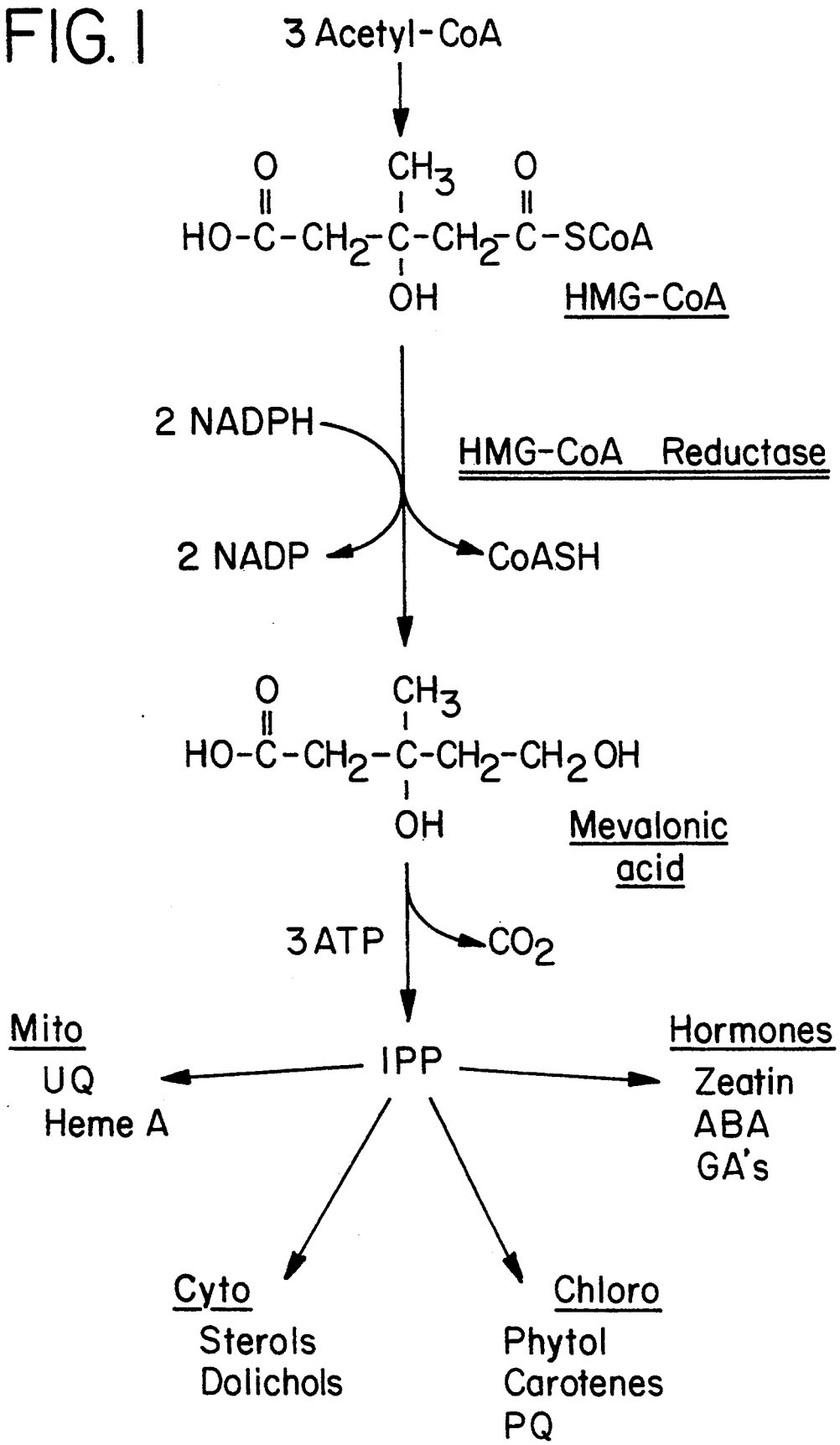
FIG. 1 is a schematic representation of the metabolism of acetyl coenzyme A to sterols and other isoprenoids in plants as published by Russell, D. W. et al., *Current Topics in Plant Biochemistry*, Vol. 4, ed. by D. D. Randall et al., Univ. of Missouri (1985).

The following words and phrases have the meanings set forth below.

Expression: The combination of intracellular processes, including transcription and translation undergone by a structural gene to produce a polypeptide.

Expression vector: A DNA sequence that forms control elements that regulate expression of structural genes when operatively linked to those genes.

Operatively linked: A structural gene is covalently bonded in correct reading frame to another DNA (or RNA as appropriate) segment, such as to an expression vector so that the structural gene is under the control of the expression vector.

Promoter: A recognition site on a DNA sequence or group of DNA sequences that provide an expression control element for a structural gene and to which RNA polymerase specifically binds and initiates RNA synthesis (transcription) of that gene.

Recombinant DNA molecule: A hybrid DNA sequence comprising at least two nucleotide sequences not normally found together in nature.

Structural gene: A DNA sequence that is expressed as a polypeptide, i.e., an amino acid residue sequence.

Vector: A DNA molecule capable of replication in a cell and/or to which another DNA segment can be operatively linked so as to bring about replication of the attached segment. A plasmid is an exemplary vector.

II. The Invention

The present invention relates to compositions and methods for increasing sterol accumulation in plants, as well as to the plants that exhibit increased sterol accumulation relative to a native variety of the plant. Plants contemplated by this invention are the vascular, multicellular higher plants. Such higher plants will hereinafter be usually referred to simply as "plants". Exemplary plants are tobacco, tomato, corn, carrot, soybean, cotton, barley, arabidopsis, guayule and petunia. A preferred plant is tobacco of the strain *Nicotiana tabacum* (*N. tabacum*).

A plant contemplated by this invention is transformed with an added structural gene that encodes a polypeptide having HMG-CoA reductase activity, that encoded polypeptide being expressed in the transformed plant. An untransformed plant that is a precursor to the transformed plant is referred to herein as a "native" plant. The native and transformed plants compared are of the same type such as siblings from the same seed pod, clones from the same parent, or plants of the same strain.

Sterol production in a plant of the present invention is increased by increasing the cellular activity of the enzyme HMG-CoA reductase, which enzyme catalyzes the conversion of 3-hydroxy-3-methylglutaryl Coenzyme A (HMG-CoA) to mevalonate. As used herein, "cellular activity" means the total catalytic activity of HMG-CoA reductase in a plant cell.

Cellular HMG-CoA reductase activity is increased by increasing the copy number of a gene encoding a polypeptide having HMG-CoA reductase catalytic activity. Expression of that encoded structural gene enhances the cellular activity of that enzyme.

The copy number is increased by transforming a plant cell with a recombinant DNA molecule comprising a vector operatively linked to an exogenous DNA segment that encodes a polypeptide having HMG-CoA reductase activity, and a promoter suitable for driving the expression of said polypeptide in said plant. Such a polypeptide includes intact as well as catalytically active, truncated HMG-CoA reductase proteins.

Thus, a transformed plant cell and plant have one or more added genes that encode a polypeptide having HMG-CoA reductase activity relative to a native, untransformed plant of the same type. As such, a transformed plant can be distinguished from a native plant by standard technology such as agarose separation of DNA fragments or mRNAs followed by transfer and appropriate blotting with DNA or RNA or by use of polymerase chain reaction technology, as are well known. Relative HMG-CoA reductase activity of the transformed and native plants or cell cultures therefrom can also be compared, with a relative activity of 1.5:1 for transformed:native showing transformation.

Sterol accumulation can also be used to distinguish between native and transformed plants. A transformed plant has at least about twice the total sterol content of a native plant where a single added gene is present.

A. Structural Genes

The present invention contemplates transforming a plant with a structural gene that encodes a polypeptide having HMG-CoA reductase activity. The HMG-CoA reductase enzymes of both animal and yeast cells comprise three distinct amino acid residue sequence regions, which regions are designated the catalytic region, the membrane binding region and the linker region. The catalytic region contains the active site of the HMG-CoA reductase enzyme and comprises about forty percent of the COOH-terminal portion of intact HMG-CoA reductase enzyme. The membrane binding region contains hydrophobic amino acid residues and comprises about fifty percent of the $NH_2$-terminal portion of intact HMG-CoA reductase enzyme. The linker region connects the catalytic and membrane binding regions, and constitutes the remaining about ten percent of the intact enzyme.

As discussed in greater detail below, only the catalytic region of HMG-CoA reductase is needed herein. Thus, a structural gene that encodes a polypeptide corresponding to that catalytic region is the minimal gene required for transforming plants. However, larger enzymes and their structural genes are preferred. Thus, the present invention contemplates use of both intact and truncated structural genes that encode a polypeptide having HMG-CoA reductase activity.

A structural gene encoding a polypeptide having HMG-CoA reductase activity can be obtained or constructed from a variety of sources and by a variety of methodologies. See, e.g., Carlson, M. and Borsrein, D., Cell, 28:145 (1982); Rine, J., et al., Proc. Nat. Acad. Sci. U.S.A., 80:6750 (1983). Exemplary of such structural genes are the mammalian and yeast genes encoding HMG-CoA reductase.

The mammalian genome contains a single gene encoding HMG-CoA reductase. The nucleotide base sequence of the hamster and human gene for HMG-CoA reductase have been described. A composite nucleotide sequence of cDNA corresponding to the mRNA, as well as the derived amino acid residue sequence, for hamster HMG-CoA reductase is provided in FIG. 2, reprinted from Chin, D. J. et al., Nature, 308:613 (1984). The composite nucleotide sequence of FIG. 2, comprising about 4606 base pairs, includes the nucleotide sequence encoding the intact hamster HMG-CoA reductase enzyme.

Intact hamster HMG-CoA reductase comprises about 887 amino acid residues. A structural gene encoding an intact hamster HMG-CoA reductase enzyme of 887 amino acid residues comprises base pairs from about nucleotide position 1 to about nucleotide position 2661 of FIG. 2.

A preferred structural gene is one that encodes a polypeptide corresponding to only the catalytic region of the enzyme. Two catalytically active segments of hamster HMG-CoA reductase have been defined. Liscum, L. et al., N. Biol. Chem., 260(1):522 (1985). One catalytic region has an apparent molecular weight of 62 kDa and comprises amino acid residues from about position 373 to about position 887. A second catalytic region has an apparent molecular weight of 53 kDa segment and comprises amino acid residues from about position 460 to about position 887. The 63 kDa catalytically active segment is encoded by base pairs from about nucleotide position 1119 to about nucleotide position 2661 of FIG. 2. The 53 kDa catalytically active segment is encoded by base pairs (bp) from about nucleotide position 1380 to about nucleotide position 2661 of FIG. 2.

In a preferred embodiment, the utilized structural gene encodes the catalytic region and at least a portion of the linker region of HMG-CoA reductase. The linker region of hamster HMG-CoA reductase comprises amino acid residues from about position 340 to about position 373 or from about position 340 to about position 460, depending upon how the catalytic region is defined. These linker regions are encoded by base pairs from about nucleotide position 1020 to about nucleotide position 1119 or from about position 1020 to about position 1380 respectively of FIG. 2. The structural gene encoding the linker region is operatively linked to the structural gene encoding the catalytic region.

In one particularly preferred embodiment, a structural gene encoding a catalytically active, truncated HMG-CoA reductase enzyme can optionally contain base pairs encoding a small portion of the membrane region of the enzyme. A truncated hamster HMG-CoA reductase gene, designated HMGR-Δ227, comprising nucleotides 1–27 and 1024–2661 from FIG. 2, which encodes amino acid residues 1–9 (from the membrane binding region) and 342–887 has been used to transform cells lacking HMG-CoA reductase. The schematic structure of the transforming plasmid (pRED-227Δ) containing the truncated gene is reprinted in FIG. 4.

A structural gene encoding a polypeptide comprising a catalytically active, truncated or intact HMG-CoA reductase enzyme from other organisms such as yeast can also be used in accordance with the present invention.

Yeast cells contain two genes encoding HMG-CoA reductase. The two yeast genes, designated HMG1 and HMG2, encode two distinct forms of HMG-CoA reductase, designated HMG-CoA reductase 1 and HMG-CoA reductase 2. The nucleotide base sequences of HMG1 and HMG2 as well as the amino acid residue sequences of HMG-CoA reductase 1 and HMG-CoA reductase 2 are presented in FIG. 3, reprinted from Basson, M. E. et al., Mol. Cell Biol., 8(9):3797 (1988).

The entire HMG1 gene comprises about 3240 base pairs. Intact HMG-CoA reductase 1 comprises an amino acid sequence of about 1054 amino acid residues. Thus, the minimal portion of the HMG1 gene that encodes an intact enzyme comprises base pairs from about nucleotide position 1 to about position 3162 of FIG. 3.

The entire HMG2 gene comprises about 3228 base pairs. Intact HMG-CoA reductase 2 comprises about 1045 amino acid residues. Thus, the minimal portion of HMG2 gene that encodes intact HMG-CoA reductase 2 comprises base pairs from about nucleotide position 1 to about position 3135 of FIG. 3.

By analogy to the truncated hamster structural gene, structural genes encoding polypeptides comprising catalytically active, truncated HMG-CoA reductase enzymes from yeast can also be used in accordance with the present invention.

The catalytic region of HMG-CoA reductase 1 comprises amino acid residues from about residue 618 to about residue 1054: i.e., the COOH-terminus. A structural gene that encodes the catalytic region comprises base pairs from about nucleotide position 1854 to about position 3162 of FIG. 3.

The linker region of HMG-CoA reductase 1 comprises an amino acid sequence from about residue 525 to about residue 617. A structural gene that encodes the linker region comprises nucleotides from about position 1575 to about position 1854 of FIG. 3. A structural gene encoding a polypeptide comprising the catalytic region and at least a portion of the linker region of yeast HMG-CoA reductase 1 preferably comprises the structural gene encoding the linker region of the enzyme operatively linked to the structural gene encoding the catalytic region of the enzyme.

Also by analogy to the truncated hamster gene, a truncated HMG1 gene can optionally contain nucleotide base pair sequences encoding a small portion of the membrane binding region of the enzyme. Such a structural gene preferably comprises base pairs from about nucleotide position 1 to about position 26 and from about position 1575 to about position 3162 of FIG. 3.

A construct similar to those above from an analogous portion of yeast HMG-CoA reductase 2 can also be utilized.

It will be apparent to those of skill in the art that the nucleic acid sequences set forth herein, either explicitly, as in the case of the sequences set forth above, or implicitly with respect to nucleic acid sequences generally known and not presented herein, can be modified due to the built-in redundancy of the genetic code and non-critical areas of the polypeptide that are subject to modification and alteration. In this regard, the present invention contemplates allelic variants of structural genes encoding a polypeptide having HMG-CoA reductase activity.

The previously described DNA segments are noted as having a minimal length, as well as total overall lengths. That minimal length defines the length of a DNA segment having a sequence that encodes a particular polypeptide having HMG-CoA reductase activity. As is well known in the art, so long as the required DNA sequence is present, (including start and stop signals), additional base pairs can be present at either end of the segment and that segment can still be utilized to express the protein. This, of course, presumes the absence in the segment of an operatively linked DNA sequence that represses expression, expresses a further product that consumes the enzyme desired to be expressed, expresses a product other than the desired enzyme or otherwise interferes with the structural gene of the DNA segment.

Thus, so long as the DNA segment is free of such interfering DNA sequences, a DNA segment of the invention can be up to 15,000 base pairs in length. The maximum size of a recombinant DNA molecule, particularly an expression vector, is governed mostly by convenience and the vector size that can be accommodated by a host cell, once all of the minimal DNA sequences required for replication and expression, when desired, are present. Minimal vector sizes are well known.

B. Recombinant DNA Molecules

A recombinant DNA molecule of the present invention can be produced by operatively linking a vector to a useful DNA segment to form a plasmid such as those discussed and deposited herein. A particularly preferred recombinant DNA molecule is discussed in detail in Example 1, hereafter. A vector capable of directing the expression of a polypeptide having HMG-CoA reductase activity is referred to herein as an "expression vector".

Such expression vectors contain expression control elements including the promoter. The polypeptide coding genes are operatively linked to the expression vector to allow the promoter sequence to direct RNA polymerase binding and expression of the desired polypeptide coding gene. Useful in expressing the polypeptide coding gene are promoters that are inducible, vital, synthetic, constitutive as described by Poszkowski et al., EMBO J., 3:2719 (1989) and Odell et al., Nature, 313:810 (1985), and temporally regulated, spatially regulated, and spatiotemporally regulated as given in Chau et al., Science, 244:174–181 (1989). The promoter preferably comprises a promoter sequence whose function in regulating expression of the structural gene is substantially unaffected by the amount of sterol in the cell. As used herein, the term "substantially unaffected" means that the promoter is not responsive to direct feedback control by the sterols accumulated in transformed cells.

A promoter is also selected for its ability to direct the transformed plant cell's transcriptional activity to the structural gene encoding a polypeptide having HMG-CoA reductase activity. Structural genes can be driven by a variety of promoters in plant tissues. Promoters can be near-constitutive, such as the CaMV 35S promoter, or tissue specific or developmentally specific promoters affecting dicots or monocots. Exemplary promoters are corn sucrose synthestase 1 [Yang, N. S., et al. Proc. Natl. Acad. Sci. U.S.A., 87:4144–48 (1990)], corn alcohol dehydrogenase 1 [Vogel, J. M., et al., J. Cell Biochem., (supplement 13D, 312)(1989)], corn zein 19KD gene (storage protein) [Boston, R. S., et al., Plant Physiol., 83:742–46 (1987)], corn light harvesting complex [Simpson, J., Science, 233:34 (1986)], corn heat shock protein [O'Dell, J. T., et al., Nature, 313:810-12 (1985)], pea small subunit RuBP Carboxylase [Poulsen, C., et al., Mol. Gen. Genet., 205:193–200 (1986); Cushmore, A. R., et al., Gen. Eng. of Plants, Plenum Press, New York, 29–38 (1983)], Ti plasmid mannopine synthase [Langridge, W. H. R., et al., Proc. Natl. Acad. Sci. U.S.A., 86:3219-3223 (1989)], Ti plasmid nopaline synthase [Langridge, W. H. R., et al., Proc. Natl. Acad. Sci. U.S.A., 86:3219-3223 (1989)], petunia chalcone isomerase [Van Tunen, A. J., et al., EMBO J., 7:1257 (1988)], bean glycine rich protein 1 [Keller, B., et al., EMBO J., 8:1309-14 (1989)], CaMV 35s transcript [O'Dell, J. T., et al., Nature, 313:810-12 (1985)] and Potato patatin [Wenzler, H. C., et al., Plant Mol. Biol., 12:41-50 (1989)]. Preferred promoters are the cauliflower mosaic virus (CaMV) 35S promoter and the S-E9 promoter.

The choice of which expression vector and ultimately to which promoter a polypeptide coding gene is operatively linked depends directly on the functional properties desired, e.g. the location and timing of protein expression, and the host cell to be. transformed. These are well known limitations inherent in the art of constructing recombinant DNA molecules. However, a vector useful in practicing the present invention is capable of directing the expression of the polypeptide coding gene included in the DNA segment to which it is operatively linked.

Typical vectors useful for expression of genes in higher plants are well known in the art and include vectors derived from the tumor-inducing (Ti) plasmid of Agrobacterium tumefaciens described by Rogers et al., Meth. in Enzymol., 153:253-277 (1987). However, several other expression vector systems are known to function in plants including pCaMVCN transfer control vector described by Fromm et al., Proc. Natl. Sci. USA, 82:5824 (1985). Plasmid pCaMVCN (available from Pharmacia, Piscataway, N.J.) includes the cauliflower mosaic virus CaMV 35 S promoter.

The use of retroviral expression vectors to form the recombinant DNAs of the present invention is also contemplated. As used herein, the term "retroviral expression vector" refers to a DNA molecule that includes a promoter sequence derived from the long terminal repeat (LTR) region of a retrovirus genome.

In preferred embodiments, the vector used to express the polypeptide coding gene includes a selection marker that is effective in a plant cell, preferably a drug resistance selection marker. One preferred drug resistance marker is the gene whose expression results in kanamycin resistance, i.e., the chimeric gene containing the nopaline synthase promoter, Tn5 neomycin phosphotransferase II and nopaline synthase 3' nontranslated region described by Rogers et al., in *Methods For plant Molecular Biology*, A. Weissbach and H. Weissbach, eds., Academic Press Inc., San Diego, Calif. (1988). Another preferred marker is the assayble chloramphenicol acetyltransferase (cat) gene from the transposon Tn9.

A variety of methods has been developed to operatively link DNA to vectors via complementary cohesive termini or blunt ends. For instance, complementary homopolymer tracts can be added to the DNA segment to be inserted and to the vector DNA. The vector and DNA segment are then joined by hydrogen bonding between the complementary homopolymeric tails to form recombinant DNA molecules.

Alternatively, synthetic linkers containing one or more restriction endonuclease sites can be used to join the DNA segment to the expression vector. The synthetic linkers are attached to blunt-ended DNA segments by incubating the blunt-ended DNA segments with a large excess of synthetic linker molecules in the presence of an enzyme that is able to catalyze the ligation of blunt-ended DNA molecules, such as bacteriophage T4 DNA ligase. Thus, the products of the reaction are DNA segments carrying synthetic linker sequences at their ends. These DNA segments are then cleaved with the appropriate restriction endonuclease and ligated into an expression vector that has been cleaved with an enzyme that produces termini compatible with those of the synthetic linker. Synthetic linkers containing a variety of restriction endonuclease sites are commercially available from a number of sources including New England BioLabs, Beverly, Mass.

Also contemplated by the present invention are RNA equivalents of the above described recombinant DNA molecules.

A preferred recombinant DNA molecule utilized in accordance with the present invention is plasmid HMGRΔ227-pKYLX71.

C. Transformed Plants and Methods of Transformation

The copy number of a gene coding for a polypeptide having HMG-CoA reductase activity is increased by transforming a desired plant with a suitable vector that contains that structural gene. Expression of that gene in the transformed plant enhances the activity of HMG-CoA reductase.

Methods for transforming polypeptide coding genes into plants include Agrobacterium-mediated plant transformation, protoplast transformation, gene transfer into pollen, injection into reproductive organs and injection into immature embryos. Each of these methods has distinct advantages and disadvantages. Thus, one particular method of introducing genes into a particular plant species may not necessarily be the most effective for another plant species, but it is well known which methods are useful for a particular plant species.

Agrobacterium-mediated transfer is a widely applicable system for introducing genes into plant cells because the DNA can be introduced into whole plant tissues, thereby bypassing the need for regeneration of an intact plant from a protoplast. The use of Agrobacterium-mediated expression vectors to introduce DNA into plant cells is well known in the art. See, for example, the methods described by Fraley et al., *Biotechnology*, 3:629 (1985) and Rogers et al., *Methods in Enzymology*, 153:253-277 (1987). Further, the integration of the Ti-DNA is a relatively precise process resulting in few rearrangements. The region of DNA to be transferred is defined by the border sequences, and intervening DNA is usually inserted into the plant genome as described by Spielmann et al., *Mol. Gen. Genet.*, 205:34 (1986) and Jorgensen et al., *Mol. Gen. Genet.*, 207:471 (1987).

Modern Agrobacterium transformation vectors are capable of replication in *E. coli* as well as Agrobacterium, allowing for convenient manipulations as described by Klee et al., in *Plant DNA Infectious Agents*, T. Hohn and J. Schell, eds., Springer-Verlag, New York (1985) pp. 179-203.

Moreover, recent technological advances in vectors for Agrobacterium-mediated gene transfer have improved the arrangement of genes and restriction sites in the vectors to facilitate construction of vectors capable of expressing various polypeptide coding genes. The vectors described by Rogers et al., *Methods in Enzymology*, 153:253 (1987), have convenient multi-linker regions flanked by a promoter and a polyadenylation site for direct expression of inserted polypeptide coding genes and are suitable for present purposes.

In those plant species where Agrobacterium-mediated transformation is efficient, it is the method of choice because of the facile and defined nature of the gene transfer.

Agrobacterium-mediated transformation of leaf disks and other tissues appears to be limited to plant species that Agrobacterium naturally infects. Agrobacterium-mediated transformation is most efficient in dicotyledonous plants. Few monocots appear to be natural hosts for Agrobacterium, although transgenic plants have been produced in asparagus using Agrobacterium vectors as described by Bytebier et al., *Proc. Natl. Acad. Sci. U.S.A.*, 84:5345 (1987). Therefore, commercially important cereal grains such as rice, corn, and wheat must be transformed using alternative methods. However, as mentioned above, the transformation of asparagus using Agrobacterium can also be achieved. See, for example, Bytebier, et al., *Proc. Natl. Acad, Sci.*, 84:5345 (1987).

A plant transformed using Agrobacterium typically contains a single gene on one chromosome. Such plants are heterozygous for the added gene. A heterozygous transformant containing a single structural gene that encodes a polypeptide having HMG-CoA reductase activity is a preferred transformed plant.

More preferred is a plant that is homozygous for the added structural gene; i.e., a plant that contains two added genes, one gene on each chromosome of a chromosome pair. A homozygous transformed plant can be obtained by sexually mating (selfing) a heterozygous plant, germinating some of the seed produced and analyzing the resulting plants produced for enhanced HMG-CoA reductase activity or sterol accumulation, or both, relative to a control or a heterozygous plant. A homozygous plant exhibits enhanced HMG-CoA reductase activity and sterol accumulation.

Transformation of plant protoplasts can be achieved using methods based on calcium phosphate precipitation, polyethylene glycol treatment, electroporation, and combinations of these treatments. See, for example, Potrykus et al., *Mol. Gen. Genet.,* 199:183 (1985); Lorz et al., *Mol. Gen. Genet.,* 199:178 (1985); Fromm et al., *Nature,* 319:791 (1986); Uchimiya et al., *Mol. Gen. Genet.,* 204:204 (1986); Callis et al., *Genes and Development,* 1:1183 (1987); and Marcotte et al., *Nature,* 335:454 (1988).

Application of these systems to different plant species depends upon the ability to regenerate that particular plant species from protoplasts. Illustrative methods for the regeneration of cereals from protoplasts are described in Fujimura et al., *Plant Tissue Culture Letters,* 2:74 (1985); Toriyama et al., *Theor Appl. Genet.,* 73:16 (1986); Yamada et al., *Plant Cell Rep.,* 4:85 (1986); Abdullah et al., *Biotechnology,* 4:1087 (1986).

To transform plant species that cannot be successfully regenerated from protoplasts, other ways to introduce DNA into intact cells or tissues can be utilized. For example, regeneration of cereals from immature embryos or explants can be effected as described by Vasil, *Biotechnology,* 6:397 (1988). In addition, "particle gun" or high-velocity microprojectile technology can be utilized.

Using that latter technology, DNA is carried through the cell wall and into the cytoplasm on the surface of small metal particles as described in Klein et al., *Nature,* 327:70 (1987); Klein et al., *Proc. Natl. Acad. Sci,* U.S.A., 85:8502 (1988); and McCabe et al., *Biotechnology,* 6:923 (1988). The metal particles penetrate through several layers of cells and thus allow the transformation of cells within tissue explants.

Metal particles have been used to successfully transform corn cells and to produce fertile, stably transformed tobacco plants as described by Gordon-Kamm, W. J. et al., *The Plant Cell,* 2:603-618 (1990); Klein, T. M. et al., *Plant Physiol.* 91:440-444 (1989); Klein, T. M. et al., *Proc, Natl. Acad. Sci.* USA, 85:8502-8505 (1988); and Tomes, D. T. et al., *Plant Mol. Biol.* 14:261-268 (1990). Transformation of tissue explants eliminates the need for passage through a protoplast stage and thus speeds the production of transgenic plants.

DNA can also be introduced into plants by direct DNA transfer into pollen as described by Zhou et al., *Methods in Enzymology,* 101:433 (1983); D. Hess, *Intern Rev. Cytol.,* 107:367 (1987); Luo et al., *Plant Mol. Biol. Reporter,* 6:165 (1988). Expression of polypeptide coding genes can be obtained by injection of the DNA into reproductive organs of a plant as described by Pena et al., *Nature,* 325:274 (1987). DNA can also be injected directly into the cells of immature embryos and the rehydration of desiccated embryos as described by Neuhaus et al., *Theor. Appl. Genet.,* 75:30 (1987); and Benbrook et al., in *Proceedings Bio Expo* 1986, Butterworth, Stoneham, Mass., pp. 27-54 (1986).

The regeneration of plants from either single plant protoplasts or various explants is well known in the art. See, for example, *Methods for Plant Molecular Biology,* A. Weissbach and H. Weissbach, eds., Academic Press, Inc., San Diego, Calif. (1988). This regeneration and growth process includes the steps of selection of transformant cells and shoots, rooting the transformant shoots and growth of the plantlets in soil.

The regeneration of plants containing the foreign gene introduced by Agrobacterium from leaf explants can be achieved as described by Horsch et al., *Science,* 227:1229-1231 (1985). In this procedure, transformants are grown in the presence of a selection agent and in a medium that induces the regeneration of shoots in the plant species being transformed as described by Fraley et al., *Proc. Natl. Acad. Sci.* U.S.A., 80:4803 (1983).

This procedure typically produces shoots within two to four months and these transformant shoots are then transferred to an appropriate root-inducing medium containing the selective agent and an antibiotic to prevent bacterial growth. Transformant shoots that rooted in the presence of the selective agent to form plantlets are then transplanted to soil or other media to allow the production of roots. These procedures vary depending upon the particular plant species employed, such variations being well known in the art.

Mature regenerated plants are obtained that exhibit increased sterol accumulation due to expression of the HMG-CoA reductase polypeptide gene. Preferably, the regenerated plants are self pollinated. Otherwise, pollen obtained from the regenerated plants is crossed to seed-grown plants of agronomically important, preferably inbred lines. Conversely, pollen from plants of those important lines is used to pollinate regenerated plants. The presence of the added gene in the progeny is assessed as discussed hereinafter.

A plant of the present invention containing a desired HMG-CoA reductase polypeptide is cultivated using methods well known to one skilled in the art. Any of the transgenic plants of the present invention can be cultivated to isolate the desired sterol products they contain.

A transformed plant of this invention thus has an increased copy number of a structural gene that encodes a polypeptide having HMG-CoA reductase activity. A preferred transformed plant is heterozygous for the added HMG-CoA reductase structural gene, whereas a more preferred transformed plant is homozygous for that gene, and transmits that gene to all of its offspring on sexual mating.

A transformed plant of the invention accumulates sterols relative to a native plant, as is discussed immediately below. A transformed plant also exhibits resistance to pests such as the hornworms as is discussed hereinafter.

D. Development of Commercial Hybrid Seed

Seed from a transformed plant is grown in the field or greenhouse and self-pollinated to generate true breeding plants. The progeny from these plants become true breeding lines that are evaluated for sterol accumulation, preferably in the field, under a range of environmental conditions.

The commercial value of a plant with increased sterol accumulation is enhanced if many different hybrid combinations are available for sale. The user typically grows more than one kind of hybrid based on such differences as maturity, standability or other agronomic traits. Additionally, hybrids adapted to one part of a country are not necessarily adapted to another part because of differences in such traits as maturity, disease and herbicide resistance. Because of this, sterol accumulation is preferably bred into a large number of parental lines so that many hybrid combinations can be produced.

Adding an enhanced sterol accumulation trait to an agronomically elite line is accomplished by a variety of techniques well known to those of skill in the art. For example, parent plants that are either homozygous or heterozygous for enhanced sterol accumulation are crossed with lines having other desireable traits, such as herbicide resistance (U.S. Pat. No. 4,761,373) produce hybrids. Preferably, plants homozygous for enhanced sterol accumulation are used to generate hybrids.

For example, a plant homozygous for enhanced sterol accumulation is crossed with a parent plant having other desired traits. The progeny, which are heterozygous for enhanced sterol accumulation, are backcrossed with the parent to obtain plants having enhanced sterol accumulation and the other desired traits. The backcrossing of progeny with the parent may have to be repeated more than once to obtain a plant that possesses all desireable traits.

Alternatively, plants with the enhanced sterol accumulation trait are transformed by introducing into such plants other genes that encode and express other desireable traits or mutated as with radiation, e.g. X-rays or gamma rays, as in U.S. Pat. No. 4,616,099, whose disclosures are incorporates by reference. Thus, the present invention also contemplates mutants and genetically engineered derivatives of plants having enhanced sterol accumulation.

E. Accumulation of Sterols in Transformed Plants

The present invention provides methods for increasing the accumulation of sterols, particularly cycloartenol, in plants. This is accomplished by increasing the copy number of a gene encoding for a polypeptide having HMG-CoA reductase activity and subsequent expression of that encoded polypeptide.

In normal, non-transformed plants sterol accumulation is equal to about 0.3 weight percent of the dry weight on the plant. The predominant sterols accumulated by such normal plants are campesterol, sitosterol, stigmasterol and derivatives of cholesterol. These sterols, $\Delta 5$-derivatives of cycloartenol that have undergone desaturation of the 5(6) carbon-carbon bond of cycloartenol, comprise over 80 weight percent of total sterols in normal plants. Cycloartenol normally comprises from about 3 to about 30 percent of the total sterols present in a plant.

Plants having an increased Copy number of a gene encoding a polypeptide having HMG-CoA reductase activity demonstrate a marked increase in total sterol accumulation. Further, the predominant sterol found in such plants is cycloartenol, which represents from about 60 to about 70 weight percent of total sterols of a transformed plant.

Thus, the present invention provides plants that over accumulate sterols relative to a native plant. Transformed heterozygous plants accumulate total sterol to a level about twice that found in native untransformed plants. In particular, transformed heterozygous plants accumulate cycloartenol to a level from about ten to about one hundred times greater than found in native plants.

These results are surprising and unexpected in light of studies relating HMG-CoA reductase activity and sterol accumulation in other organisms.

In yeast, increases in HMG-CoA reductase activity are associated with increases in squalene (a sterol precursor), 4,14-dimethylzymosterol and 14-methylfecosterol (analogous to the $\Delta 5$-sterols of plants). Downing, J. F. et al., *Biochemical and Biophysical Research Communications*, 94(3): 974–979(1980). Increases in HMG-CoA reductase activity of yeast were not associated with increases in lanosterol, (a sterol of yeast analogous to cycloartenol). Benveniste, P., *Ann. Rev. Plant Physiol.*, 37:275–308 (1986).

In non-photosynthetic microorganisms, increases in HMG-CoA reductase activity were not associated with increases in sterol accumulation. Tada, M. and Shiroishi, M. *Plant and Cell Physiology*, 23 (4): 615–621(1982).

F. Harvesting of Sterols

If desired, after cultivation, the transgenic plant is harvested to recover the sterol product. This harvesting step can consist of harvesting the entire plant, or only the leaves, or roots of the plant. This step can either kill the plant or, if only a non-essential portion of the transgenic plant is harvested, can permit the remainder of the plant to continue to grow.

In preferred embodiments this harvesting step further comprises the steps of:

(i) homogenizing at least a sterol-containing portion of the transgenic plant to produce a plant pulp and using the sterol-containing pulp directly, as in dried pellets or tablets as where an animal food is contemplated; or (ii) extracting the sterol(s) from the plant pulp with an appropriate solvent such as an organic solvent or by supercritical extraction [Favati et al., *J. Food Sci.*, 53:1532 (1988) and the citations therein] to produce a sterol-containing liquid solution or suspension; and (iii) isolating the sterol(s) from the solution or suspension.

At least a portion of the transgenic plant is homogenized to produce a plant pulp using methods well known to one skilled in the art. This homogenization can be done manually, by a machine, or by a chemical means as long as the transgenic plant portions are broken up into small pieces to produce a plant pulp. This plant pulp consists of a mixture of the sterol of interest, residual amounts of precursors, cellular particles and cytosol contents. This pulp can be dried and compressed into pellets or tablets and eaten or otherwise used to derive the benefits, or the pulp can be subjected to extraction procedures.

The sterol can be extracted from the plant pulp produced above to form a sterol-containing solution or suspension. Such extraction processes are common and well known to one skilled in this art. For example, the extracting step can consist of soaking or immersing the plant pulp in a suitable solvent. This suitable solvent is capable of dissolving or suspending the sterol present in the plant pulp to produce a sterol-containing solution or suspension. Solvents useful for such an extraction process are well known to those skilled in the art and include several organic solvents and combinations thereof such as methanol, ethanol, isopropanol, acetone, acetonitrile, tetrahydrofuran (THF), hexane, and chloroform as well as water-organic solvent mixtures. A vegetable oil such as peanut, corn, soybean and similar oils can also be used for this extraction.

A plant transfected with a structural gene for a polypeptide having HMG-CoA reductase activity is grown under suitable conditions for a period of time sufficient for sterols to be synthesized. The sterol-containing plant cells, preferably in dried form, are then lysed chemically or mechanically, and the sterol is extracted from the lysed cells using a liquid organic solvent, as described before, to form a sterol-containing liquid solution or suspension. The sterol is thereafter isolated from the liquid solution or suspension by usual means such as chromatography.

The sterol is isolated from the solution or suspension produced above using methods that are well known to those skilled in the art of sterol isolation. These methods include, but are not limited to, purification procedures based on solubility in various liquid media, chromatographic techniques such as column chromatography and the like.

G. Pest Resistance of Transformed Plants

Certain sterols accumulated by the transformed plants of the present invention have use as systemic pesticidal agents. This embodiment of the present invention relates to a method of increasing pest resistance of a plant comprising transforming a native plant with a recombinant DNA molecule comprising a vector operatively linked to an exogenous DNA segment that encodes the catalytic region of HMG-CoA reductase, and a promoter suitable for driving the expression said reductase in said plant. In preferred practice, the exogenous DNA segment also encodes at least a portion of the linker region but not the membrane binding region of HMG-CoA reductase. Use of the hamster gene is particularly preferred.

Tobacco hornworm larvae grown on the leaves of plants transformed with a truncated hamster HMG-CoA reductase gene, which plants have increased levels of cyclartenol, demonstrated retarded development. Preliminary studies also indicate that boll worms fed on leaves of a similarly transformed plant had retarded development under similar condition.

The following examples illustrate the best mode of carrying out the invention and are not to be construed as limiting of the specification and claims in any way.

Best Mode for Carrying Out the Invention

EXAMPLE 1: Transformation of Plant Cells

Plant cells were transformed in accordance with standard methods for expressing foreign genes in plants. Schardl, C. L., et al. *Gene* 61:1-11 (1987). A pKYLX series of vectors was used as the expression system. Preferred vectors are plasmids pKYLX6 and pKYLX7. Berger, P. J., et al., *Proc. Natl. Acad. Sci.* USA, 86: 8402-8406 (1989).

Transformations were performed with a truncated Hamster HMG-CoA reductase gene (HMGR-$\Delta$227) obtained from the laboratories of Dr. J. L. Goldstein, See, e,g., Gil, G. et al., *Cell*, 41: 249-258(1985); Bard, M. and Downing, J. F. *Journal of General Microbiology*, 125:415-420(1981).

The HMGR-$\Delta$227 gene was incorporated into modified vectors pKYLX6 (an *E. coli* vector designed for intermediate constructs) and pKYLX7 (an *A. tunefaciens* vector designed for integration of cloned genes). Berger, P. J., et al., *Proc. Natl. Acad. Sci.* USA, 86: 8402-8406 (1989). The modified vectors pKYLX61 and pKYLX71 contained Hind III, Xho I, Bam HI, Pst I, and Sst I sites in place of the original Hind III Sst I fragment multiple cloning site region.

The HMGR-$\Delta$227 gene was digested with Bam HI and Sst I, and the approximately, 2500 bp HMGR-$\Delta$227-Bam HI-Sst I fragment was inserted into plasmid pKYLX61. The resulting HMGR$\Delta$227-pKYLX61 construct was cleaved with Eco RI and Cla I, and an approximately 4000 bp fragment containing the promoter-gene-terminator was inserted into corresponding sites of pKYLX71 to generate plasmid HMGR$\Delta$227-pKYLX71 (see FIG. 6). In plasmid HMGR$\Delta$227-KYLX71, the truncated HMGR-$\Delta$227 gene is under control of the strong, constitutive CaMV35S promoter.

The MMGR$\Delta$227-pKYLX71 plasmid was mobilized into *Agrobacterium tumefaciens* by a standard triparental mating between *E. coli*, harboring the MMGR$\Delta$227-pKYLX71 construct, *Agrobacterium tumefaciens*, harboring a disarmed Ti-plasmid, GV3850, and *E. coli* harboring the conjugation helper plasmid pRK2013. See, e.g., Schardl, et al., Supra; Ditta, G. et al., *Proc. Natl. Acad. Sci.* USA 77:7347-7351 (1980). As a result of the cross, Agrobacterium harboring the HMGR$\Delta$227-pKYLX71 construct, was selected for by resistance to rifampicin (encoded on the chromosome of Agrobacterium), and to tetracycline and kanamycin (encoded on the pKYLX71 vector).

*Nicotiana tabacum* L. cv. xanthii (*N. tabacum*) was transformed by the well known "leaf disk method". Horsch, R. B., et al., *Science* 27:1229-1231 (1985). Leaf disks were incubated with Agrobacteria containing $\Delta$227-pKYLX71 for about 3 days. Transformed tissue was selected for by resistance to kanamycin (encoded by the pKYLX71 vector), cured of Agrobacteria using the antibiotic mefoxin, and regenerated into whole plants. Horsch, R. B., et al., *Science* 27:1229-1231 (1985).

Plant tissue was checked for the presence of integrated copies of the HMGR $\Delta$227 gene sequences by the method of Mettler, *Plant Mol. Biol., Reporter* 5:346-349 (1987). RNA transcription levels were determined by northern blotting or S-1 protection assays. Maniatis, T., et al., *Molecular Cloning: A Laboratory Manual*, Cold Spring Harbour Lab., Cold Spring Harbour, N.Y. (1982).

Plants exhibiting HMG-CoA reductase activity greater than control plants [untransformed (native) or transformed without the HMGR-$\Delta$227-construct] were sexually crossed with themselves, to generate progeny.

EXAMPLE 2: HMG-CoA Reductase Enzyme Activity in Transgenic Plants

Transgenic plants were screened for expression of the truncated HMGR gene by examining HMG-CoA reductase activity in the 100,000 xG supernatant of lysed cells using a standard assay, Chappel, J., and Nable, R., *Plant Physiol.* 85:469-473 (1987).

Soluble HMG-CoA reductase enzyme activity was measured in callus cultures grown on selection (kanamycin) medium, seedlings germinated in the presence of kanamycin or on moistened filter paper, and leaves of various sizes from plants grown in the greenhouse. Results of studies of HMG-CoA reductase activity in leaves from greenhouse-grown plants are also summarized in Table 1 below:

TABLE 1

| Plant Sample No. | Total HMG-CoA Reductase Activity (pmol/hr./leaf) | % of Control |
| --- | --- | --- |
| Control | | |
| 30 | 258 | 100 |
| Transformed | | |
| 5 | 860 | 300 |
| 14 | 1,100 | 390 |
| 15 | 633 | 220 |
| 18 | 456 | 160 |
| 23 | 713 | 250 |

The control plant, 30, was transformed with a selection marker but not with the $\Delta$227 gene. Plants 5, 14, 15, 18 and 23 (independently transformed) were transformed with the HMGR-Δ227 gene.

Total HMG-CoA reductase activity was 1.6 to 3.9 times greater in plants harboring the Δ227 gene as compared to the control plant.

EXAMPLE 3: Sterol Accumulation in Transformed Plants

*N. tabacum*, transformed with the HMGR-Δ227 gene according to the method of Example 1 were analyzed for total sterol content. Sterols were measured by analytical gas chromatography using an internal standard. The results are presented in Table 2.

TABLE 2

| Plant Sample | HMG-CoA Reductase (pmol mg dry wt.) | Total Sterols (% of dry wt) |
|---|---|---|
| Control Plants (n = 6) | 2.00 ± 0.19 | 0.27 ± 0.02 |
| Transformed Plants (n = 12) | 5.75 ± 1.55 | 0.89 ± 0.17 |

Transformed plants had elevated HMG-CoA reductase activity and increased sterol content.

In addition to determining total sterol content, transformed *N. tabacum* were examined for the accumulation of specific sterols. The results of such an analysis in a control (Cntrl) and HMGR-Δ227 transformed (Trf) plant are presented in Table 3.

TABLE 3

| | Percent Dry weight of Sterols | | | | | |
|---|---|---|---|---|---|---|
| | Callus | | Leaf | | Root | |
| Sterols | Cntrl | Trf | Cntrl | Trf | Cntrl | Trf |
| Campesterol | 0.009 | 0.021 | 0.057 | 0.056 | 0.058 | 0.022 |
| Cholesterol | 0.004 | tr | tr | tr | | |
| Cycloartenol | 0.003 | 0.258 | 0.011 | 0.678 | 0.039 | 0.642 |
| Sitosterol | 0.027 | 0.077 | 0.083 | 0.187 | 0.029 | 0.194 |
| Stigmasterol | 0.003 | 0.012 | 0.132 | 0.078 | tr | 0.238 | tr = trace (<0.001% dry wt.)

In the control plant, cycloartenol represented from about 3(0.011/0.283 percent dry weight) (leaf) to about 30(0.039/0.126 percent dry weight) (root) percent of total sterol accumulation. The predominant sterols accumulated by control plants (i.e. sitosterol, campesterol) are Δ5-sterol derivatives of cycloartenol that have undergone additional metabolic transformation.

As a result of transformation with the HEMGR-Δ227 gene, the ratio of cycloartenol to its derivatives is reversed. In transformed plants, cycloartenol accumulation represents from about 60 (root) to about 70 (leaf) percent by weight of total sterol accumulation.

These data show that transformed plants of the present invention over accumulate sterols relative to a native, untransformed plant. Transformed, heterozygous plants over accumulate total sterols to a level about twice that found in a native plant. The data further show that transformed heterozygous plants over accumulate cycloartenol to a level about ten to about one hundred times greater than found in a native plant.

EXAMPLE 4: Insecticidal Effects of Transformed Plants

First instar larvae of the tobacco pests Tobacco Hornworm or Manduca Sexta, were placed onto leaves of control or HMGR-Δ227 transformed *N. tabacum* on a moistened filtered paper in a petri dish. Additional leaf material, from control or transformed plants, was added to each dish, and the larvae were grown for an additional 7 days. Larvae were then examined to determine growth and development. The results are presented in Table 4.

TABLE 4

| | Control | Transformed |
|---|---|---|
| Development | | |
| % of larvae in second instar | 28.6 | 100 |
| % of larvae in premolt or third instar | 71.4 | 0 |
| Growth | | |
| Fresh Wet Weight (mg) | 42.8 | 24.4 |

Tobacco Hornworm or Manduca Sexta larvae grown on leaves from HMGR-Δ227-transformed plants demonstrated retarded development (no progression beyond the second instar stage) and inhibited growth (wet weight) as compared to controls. The cycloartenol levels of the control and transformed plants used in this study were 0.017 and 1.02 percent of dry leaf weight, respectively. This study thus illustrates both the method of increasing the accumulation of cycloartenol in a plant and of enhancing pest resistance in a plant.

Preliminary studies with a member of the heliothus group of insect pests, the boll worm, indicate a slower growth rate for insects fed on leaves of transformed plant 14 (Example 2) than on leaves of the native, control plant 30 (Example 2). An effect on the fecundity of the insects fed on either type of leaf was also noted.

EXAMPLE 5: Homozygous Transformed Plants

The previously described transformed plants were heterozygous for the introduced HMG-CoA reductase gene. One of those plants, plant 14 of Example 2, was selfed; i.e., sexually mated with itself.

Twelve seeds from that cross were germinated and raised into plants. The tissues of those siblings were then analyzed for HMG-CoA reductase activity, total protein and total sterol content. The specific activity of HMG-CoA reductase was also calculated. The results of that assay compared to similar data from siblings from a selfing of plant 30 (Example 2) are presented in Table 5, below.

TABLE 5

| Plant | HMGR Activity[1] | Protein[2] | Specific Activity[3] | Sterols[4] |
|---|---|---|---|---|
| 30-1 | 3.78 | 30.22 | 184 | 0.20 |
| 30-2 | 2.20 | 30.00 | 146 | 0.25 |
| 30-3 | 1.44 | 18.70 | 154 | 0.29 |
| 30-4 | 2.13 | 23.67 | 180 | 0.31 |
| 30-5 | 1.70 | 19.27 | 176 | 0.36 |
| 30-6 | 1.77 | 19.32 | 183 | 0.22 |
| 14-1 | 1.36 | 23.60 | 115 | 0.21 |
| 14-2 | 2.07 | 26.55 | 156 | 0.17 |
| 14-3 | 10.28 | 17.60 | 1168 | 1.10 |
| 14-4 | 7.08 | 27.25 | 520 | 0.74 |
| 14-5 | 4.13 | 20.92 | 394 | 1.59 |
| 14-6 | 1.58 | 11.00 | 143 | 0.25 |
| 14-7 | 20.35 | 16.77 | 2,426 | 2.05* |
| 14-8 | 4.87 | 24.20 | 402 | 0.97 |
| 14-9 | 2.37 | 12.95 | 366 | 0.19 |
| 14-10 | 7.94 | 11.00 | 1,444 | 1.02 |
| 14-11 | 2.56 | 15.25 | 334 | 1.10 |

TABLE 5-continued

| Plant | HMGR Activity[1] | Protein[2] | Specific Activity[3] | Sterols[4] |
|---|---|---|---|---|
| 14-12 | 4.39 | 21.10 | 416 | 1.29 |

[1]pmoles/0.5 hours.
[2]micrograms (mg).
[3]pmoles of enzyme/hour/mg of total protein.
[4]percentage of dry weight.
*this plant died.

On the basis of the above data, the plants were classified as to (a) having no added MMG-CoA reductase gene, (b) being heterozygous for the added gene, as was plant 14, or (c) homozygous for the added gene. Illustratively, plant 14-2 was thus determined to be heterozygous for the added gene, plant 14-6 was determined to be heterozygous for the added gene and plant 14-8 was determined to be homozygous for the added gene; i.e., it contained an added gene on each of two chromosomes.

These data show that seeds from a transformed plant are capable of germinating into a plant capable of expressing enhanced sterol accumulation due to an increased copy number of gene encoding a polypeptide having HMG-CoA reductase activity.

Taken together with the data of Example 3, these data show that the transformed plants of the present invention over accumulate sterols relative to a native plant and that such plants are capable of producing seeds, which germinate into plants that over accumulate sterols.

Seeds from a selfing of plant 14-8 were deposited pursuant to the Budapest Treaty requirements with the American Type Culture Collection (ATCC) at 12301 Parklawn Drive, Rockville, Md. 20852 U.S.A. on Sep. 28, 1990, and were assigned accession number ATCC 40904.

The present invention has been described with respect to preferred embodiments. It will be clear to those skilled in the art that modifications and/or variations of the disclosed subject matter can be made without departing from the scope of the invention set forth herein.

We claim:

1. A DNA construct comprising a structural gene, said structural gene consisting essentially of nucleotides encoding an HMG-CoA reductase enzyme catalytic region and at least a portion of the HMGCo-A linker region, and further comprising a promoter operably linked to said structural gene, said DNA construct being operable in plants.

2. A DNA construct according to claim 1 wherein the promoter is a promoter whose regulatory function is substantially unaffected by the level of sterol in the plant.

3. A DNA construct according to claim 2 wherein the promoter is the CaMV35S promoter.

4. A DNA construct according to claim 2 wherein the DNA construct is plasmid HMGRΔ227-pKYLX71.

5. A plant that is the progeny of a plant transformed with a DNA construct, said DNA construct comprising a structural gene, said structural gene consisting essentially of nucleotides encoding an HMG-CoA reductase enzyme catalytic region and at least a portion of the HMGCo-A linker region, said progeny plant containing said DNA construct and overaccumulating sterol and cycloartenol in comparison to a native plant that is not the progeny of a transformed plant.

6. Hybrid plants which have at least one parent plant according to claim 5, said hybrid plant overaccumulating sterol and cycloartenol in comparison to a native plant which is not the progeny of a transformed plant.

7. A plant whose genome contains transgenic DNA comprising a structural gene, said transgenic structural gene consisting essentially of nucleotides encoding an HMG-CoA reductase enzyme catalytic region and at least a portion of the HMGCo-A linker region, said plants overaccumulating sterol and cycloartenol in comparison to native plants not containing said structural gene.

8. A seed which will germinate into a plant of claim 7.

9. A process of producing a plant which overaccumulates sterols relative to a native, non-transformed plant comprising crossing a plant according to claim 7 with a non-transformed plant.

10. A plant according to claim 7 selected from the group consisting of: tobacco, tomato, corn, carrot, soybean, cotton, barley, arabidopsis, guayule, and petunia.

11. A plant according to claim 5 selected from the group consisting of: tobacco, tomato, corn, carrot, soybean, cotton, barley, arabidopsis, guayule, and petunia.

* * * * *